US011382506B2

(12) United States Patent
DeAyala et al.

(10) Patent No.: US 11,382,506 B2
(45) Date of Patent: Jul. 12, 2022

(54) RETINAL IMAGING SYSTEM

(71) Applicant: Ai-Ris LLC, College Station, TX (US)

(72) Inventors: Marcus Emilio DeAyala, College Station, TX (US); Tokunbo Said Falohun, College Station, TX (US); Daniel Shafiee Kermany, College Station, TX (US); Harsha Kalkunte Mohan, College Station, TX (US); Uthej Vattipalli, College Station, TX (US); Amir Tofighi Zavareh, College Station, TX (US)

(73) Assignee: Ai-Ris LLC, College Station, TX (US)

( * ) Notice: Subject to any disclaimer, the term of this patent is extended or adjusted under 35 U.S.C. 154(b) by 0 days.

(21) Appl. No.: 17/489,342

(22) Filed: Sep. 29, 2021

(65) Prior Publication Data
US 2022/0095911 A1 Mar. 31, 2022

Related U.S. Application Data

(60) Provisional application No. 63/085,837, filed on Sep. 30, 2020.

(51) Int. Cl.
*A61B 3/12* (2006.01)
*H04N 5/33* (2006.01)
(Continued)

(52) U.S. Cl.
CPC .............. *A61B 3/12* (2013.01); *A61B 3/0008* (2013.01); *A61B 3/0091* (2013.01); *A61B 3/156* (2013.01);
(Continued)

(58) Field of Classification Search
CPC ....... A61B 3/12; A61B 3/0008; A61B 3/0091; A61B 3/156; A61B 5/6803; A61B 5/7267; G06K 9/6256; H04N 5/33
(Continued)

(56) References Cited

U.S. PATENT DOCUMENTS

| 2015/0098620 | A1 | 4/2015 | Wu et al. | |
| 2015/0205347 | A1* | 7/2015 | Border | G06F 3/013 345/156 |

(Continued)

FOREIGN PATENT DOCUMENTS

WO 2020/023959 1/2020

OTHER PUBLICATIONS

International Search Report and Written Opinion issued in corresponding International Patent Application No. PCT/JS2021/052675, dated Jan. 25, 2022.
(Continued)

*Primary Examiner* — Mohammed A Hasan
(74) *Attorney, Agent, or Firm* — Pillsbury Winthrop Shaw Pittman, LLP

(57) ABSTRACT

Provided is a wearable fundus camera configured to be worn as a headset by a human, the wearable fundus camera comprising: an infrared light source configured to output infrared light to be directed at a retina of the human; an image sensor configured to capture infrared images depicting a retina of an eye of the human under illumination from the infrared light source without a pupil of the eye being dilated with mydriatics; and an eye cuff configured to be biased against a face of the human and occlude at least some ambient light from reaching the image sensor.

22 Claims, 15 Drawing Sheets

(51) Int. Cl.
  *G06K 9/62* (2022.01)
  *A61B 3/00* (2006.01)
  *A61B 5/00* (2006.01)
  *A61B 3/15* (2006.01)

(52) U.S. Cl.
  CPC .......... *A61B 5/6803* (2013.01); *A61B 5/7267* (2013.01); *G06K 9/6256* (2013.01); *H04N 5/33* (2013.01)

(58) Field of Classification Search
  USPC ........................................................ 351/206
  See application file for complete search history.

(56) References Cited

U.S. PATENT DOCUMENTS

| | | | |
|---|---|---|---|
| 2017/0265798 A1* | 9/2017 | Sales | G06V 20/35 |
| 2017/0357879 A1 | 12/2017 | Ddaibo et al. | |
| 2018/0140187 A1 | 5/2018 | Watanabe et al. | |
| 2019/0110753 A1 | 4/2019 | Zhang et al. | |
| 2019/0206054 A1 | 7/2019 | Mao et al. | |
| 2020/0074622 A1 | 3/2020 | Fang et al. | |
| 2020/0085290 A1 | 3/2020 | Wang et al. | |
| 2020/0160521 A1 | 5/2020 | Wang et al. | |
| 2020/0196853 A1 | 6/2020 | Van Hemert et al. | |
| 2020/0245873 A1* | 8/2020 | Frank | A61B 5/0823 |
| 2020/0311933 A1 | 10/2020 | Semturs et al. | |
| 2020/0356805 A1 | 11/2020 | Sun et al. | |
| 2020/0390392 A1* | 12/2020 | Hallack | A61B 5/1176 |
| 2021/0224997 A1 | 7/2021 | Kushida et al. | |
| 2021/0235984 A1 | 8/2021 | Scheibler et al. | |
| 2021/0244274 A1 | 8/2021 | Claggett | |
| 2021/0259546 A1 | 8/2021 | Santos et al. | |
| 2021/0275009 A1 | 9/2021 | Fates | |
| 2021/0290050 A1 | 9/2021 | Shiba et al. | |
| 2021/0295508 A1 | 9/2021 | Shiba et al. | |

OTHER PUBLICATIONS

Dosovitskiy, A., et al., "An Image is Worth 16X16 Words: Transformers for Image Recognition at Scale." [online] Conference paper at ICLR 2021, Jun. 3, 2021 [retrieved on Sep. 30, 2021]. Retrieved from the internet.

Tolstikhin, I., et al., "MLP-Mixer: An all-MLP Architecture for Vision." [online] May 4, 2021 [retrieved on Sep. 30, 2021]. Retrieved from the internet.

* cited by examiner

RETINAL IMAGING SYSTEM

CROSS-REFERENCE TO RELATED APPLICATIONS

This application claims the priority to U.S. Provisional Patent Application 63/085,837, titled "Retinal Imaging System," which was filed on 30 Sep. 2020. The disclosure of each afore-listed patent filing is incorporated herein by reference in its entirety.

BACKGROUND

1. Field

The present disclosure relates generally to medical devices and, more specifically, to retinal imaging systems.

2. Description of the Related Art

Ophthalmologists and other medical professionals use a variety of tools to assess eye health. For example, ophthalmoscopes, or fundoscopes, are used to non-invasively view the fundus of the eye, which is the eye's interior surface opposite the lens. Visual assessments of the fundus can be used to assess the health of the retina, optical disc, and vitreous humor, among other uses. In some cases, the pupil is dilated before such assessments, or for convenience, un-dilated examination may be performed, albeit under more challenging conditions in some cases.

SUMMARY

The following is a non-exhaustive listing of some aspects of the present techniques. These and other aspects are described in the following disclosure.

Some aspects include light-weight, low-cost, wearable fundus camera paired with a trained computer vision model operative to classify retinal images according to whether the retinal images depict retinopathy or other abnormalities.

Some aspects include a tangible, non-transitory, machine-readable medium storing instructions that when executed by a data processing apparatus cause the data processing apparatus to perform a method of operating of the above-described camera or model.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
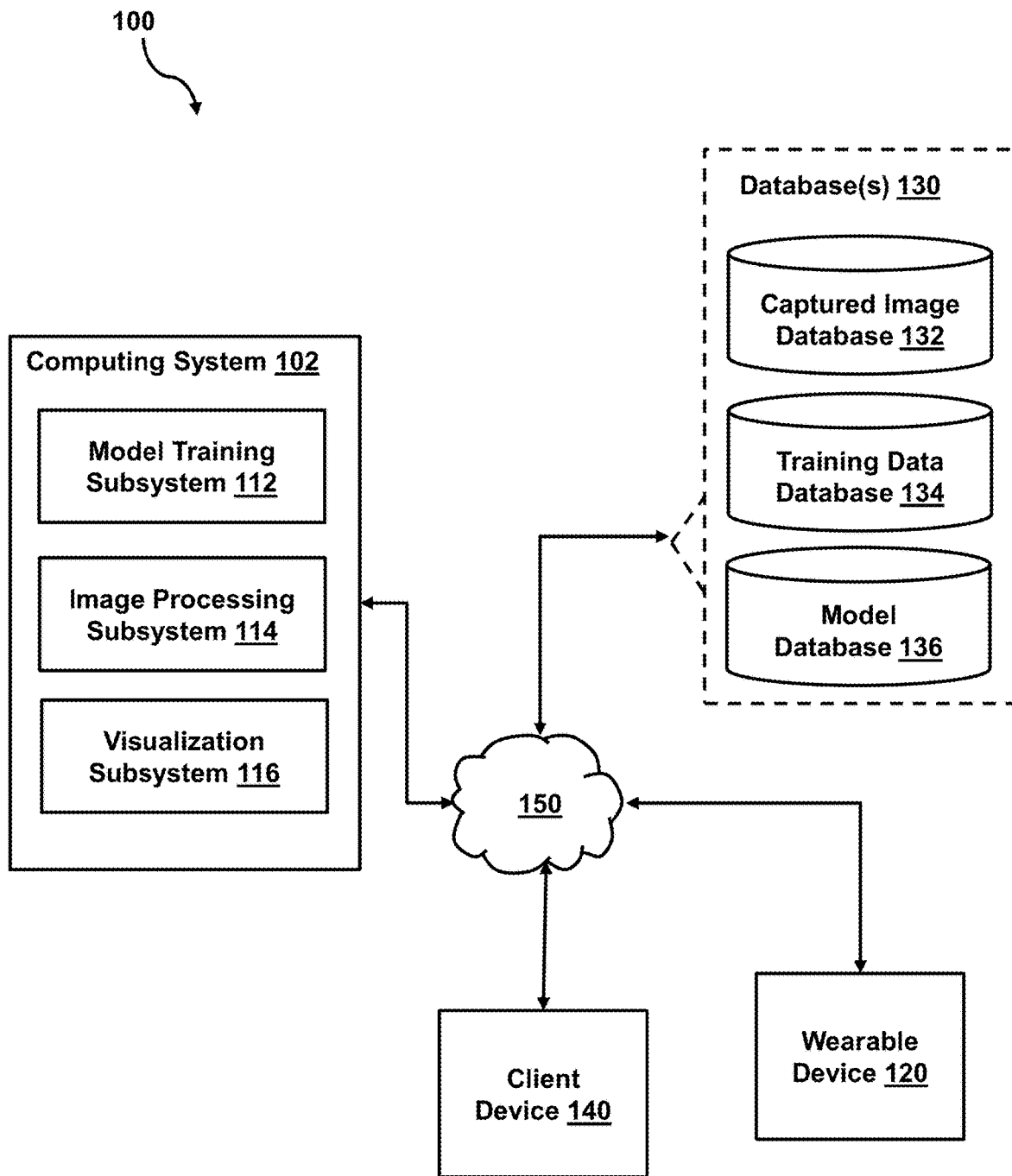
FIG. 1 illustrates an example system for determining whether a retina of an eye of a patient includes a retinal abnormality, in accordance with various embodiments.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the fields of computer vision and medical-device engineering. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Ocular diseases, such as diabetic retinopathy and glaucoma, can lead to irreversible vision loss and blindness. These diseases are further exacerbated in rural areas and underserved communities, where access to medical care is limited. With the use of machine learning models and low-cost hardware, some embodiments mitigate this challenge by assisting individuals in their efforts to monitor the condition of their eye in the absence of a medical professional, sophisticated medical equipment, or both. By improving the ease of access to eye exams, patients suffering from ocular diseases are expected to be better able to monitor and preserve their vision. To these ends and others, some embodiments include a relatively low-cost camera and embedded processor (e.g., leveraging a camera and processor of a smartphone or headset) in the creation of a portable ophthalmoscope to diagnose ocular diseases. Some embodiments include an apparatus configured to optically interface between the camera and the subject's eye, some embodiments include program code fixed in a tangible media that can analyze resulting images, and some embodiments include both of these components.

Some embodiments include a portable headset that contains optical and electronic components that provide the ability to visualize and automatically evaluate the condition of a patient's retina without the need to dilate the pupil using mydriatic therapeutic agents, such as tropicamide. Some embodiments contain both hardware and software components to allow for automatic screening of a patient's retina for ocular diseases such as diabetic retinopathy, glaucoma, and age-related macular degeneration.

In some cases, physical properties of the portable headset (such as wearable device 120 described below) are expected to facilitate lower-cost, more widely deployed devices. For example, some embodiments have a relative low weight, e.g., less than 4 kg, such as less than 2 kg, like between 200 grams and 1 kg, and some embodiments may have a center of mass relatively close to the user's face, e.g., within less than 10 cm, like between 1 and 5 cm forward from a portion of an eyecup configured to be placed adjacent a bridge of the user's nose. Together, these physical properties are expected to reduce rotational inertia of the headset and allow the headset to physical exhibit relatively little movement relative to the user's head during imaging, even when the user moves. This approach is expected to facilitate capture of relatively high-quality images even without using more expensive adaptive optical systems or having the user attached to a heavy table-top imaging device. That said, embodiments are not limited to systems that afford these benefits, which is not to suggest that any other description is limiting.

Illumination of the fundus may be done using infrared (IR) light (e.g., with a wavelength between around 700 nm and 12 micron), which is not visible to the human eye, but can be detected using an infrared camera, which may be used for image detection. This allows for fundus imaging in complete darkness, where the pupils of the eye naturally dilate. To this end, a headset may block light (e.g., more than 50%, more than 90%, or more than 99% of ambient light) from reaching the patient's eye, thus evoking mydriasis, or the eye dilation response, without the need for medication. Once the infrared image is captured, the image may processed through a software algorithm. IR light may include near IR (NIR) light, which represents a portion of the infrared spectrum (e.g., with a wavelength between around 700 nm and 1 micron) closest to the visible spectrum (e.g., with a wavelength between around 300 nm and 700 nm).

In some embodiments, the retina imaging system may include an illumination system. Infrared light, generated from LEDs (e.g., 850 or 920 nm, 1050 nm, 1310 nm wavelength light-emitting diodes), or from other infrared light sources, may be positioned to illuminate a light-exclusion volume of the headset, to thereby illuminate the fundus; thus providing the ability to visualize elements of the patient's retina to allow for image capturing. In operation, the illumination system may be used to project intense infrared light onto the patient's retina. These incident infrared light may enter a patient's eye through their pupil and illuminate their retina. The illumination can be of a continuous spectrum of light or a single or multiple discrete spectral frequency of light. Different frequencies of light (e.g., IR light) may be illuminated at the same time or at different times (e.g., to capture multiple images with different types of IR light, in some cases, with varying apertures). In some cases, off-axis illumination applied at different times, structured light, or stereoscopic imaging may also be used to capture images from which depth may be inferred.

FIG. 1 illustrates an example system for determining whether a retina of an eye of a patient includes a retinal abnormality, in accordance with various embodiments. In some embodiments, system 100 may include computing system 102, wearable device 120 (such as a wearable fundus camera), databases 130, client device 140, or other components. Computing system 102, wearable device 120, and client device 140 may communicate with one another via network 150 (or in some cases, some or all of computing system 102 may be integrated with the wearable device 120). Although a single instance of computing system 102, wearable device 120, and client device 140 are represented within system 100, multiple instances of computing system 102, wearable device 120, or client device 140 may be included within system 100, and a single instance of each is illustrated to minimize obfuscation within FIG. 1. For example, system 100 may include multiple wearable devices, multiple client devices, multiple computing systems, or other components.

Network 150 may be a communications network including one or more Internet Service Providers (ISPs). Each ISP may be operable to provide Internet services, telephonic services, or other services, to one or more components of system 100. In some embodiments, network 150 may facilitate communications via one or more communication protocols, such as, TCP/IP, HTTP, WebRTC, SIP, WAP, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS 136/TDMA, iDen, LTE or any other suitable cellular network protocol), infrared, BitTorrent, FTP, RTP, RTSP, SSH, VOID, or other mechanisms for facilitating communications between components of system 100.

Client device 140 may include one or more processors, memory, communications components, and/or additional components (e.g., display interfaces, input devices, etc.). Client device 140 may include any type of mobile terminal, fixed terminal, or other device. By way of example, client device 140 may include a desktop computer, a notebook computer, a tablet computer, a smartphone, a wearable device, or other client device. Users may, for instance, utilize client device 140 to interact with one another, one or more servers, or other components of system 100.

Computing system 102 may include one or more subsystems, such as model training subsystem 112, image processing subsystem 114, visualization subsystem 116, or other subsystems. Computing system 102 may include one or more processors, memory, and communications components for interacting with different aspects of system 100. In some embodiments, computer program instructions may be stored within memory, and upon execution of the computer program instructions by the processors, operations related to some or all of subsystems 112-116 may be effectuated.

Figure 2A:
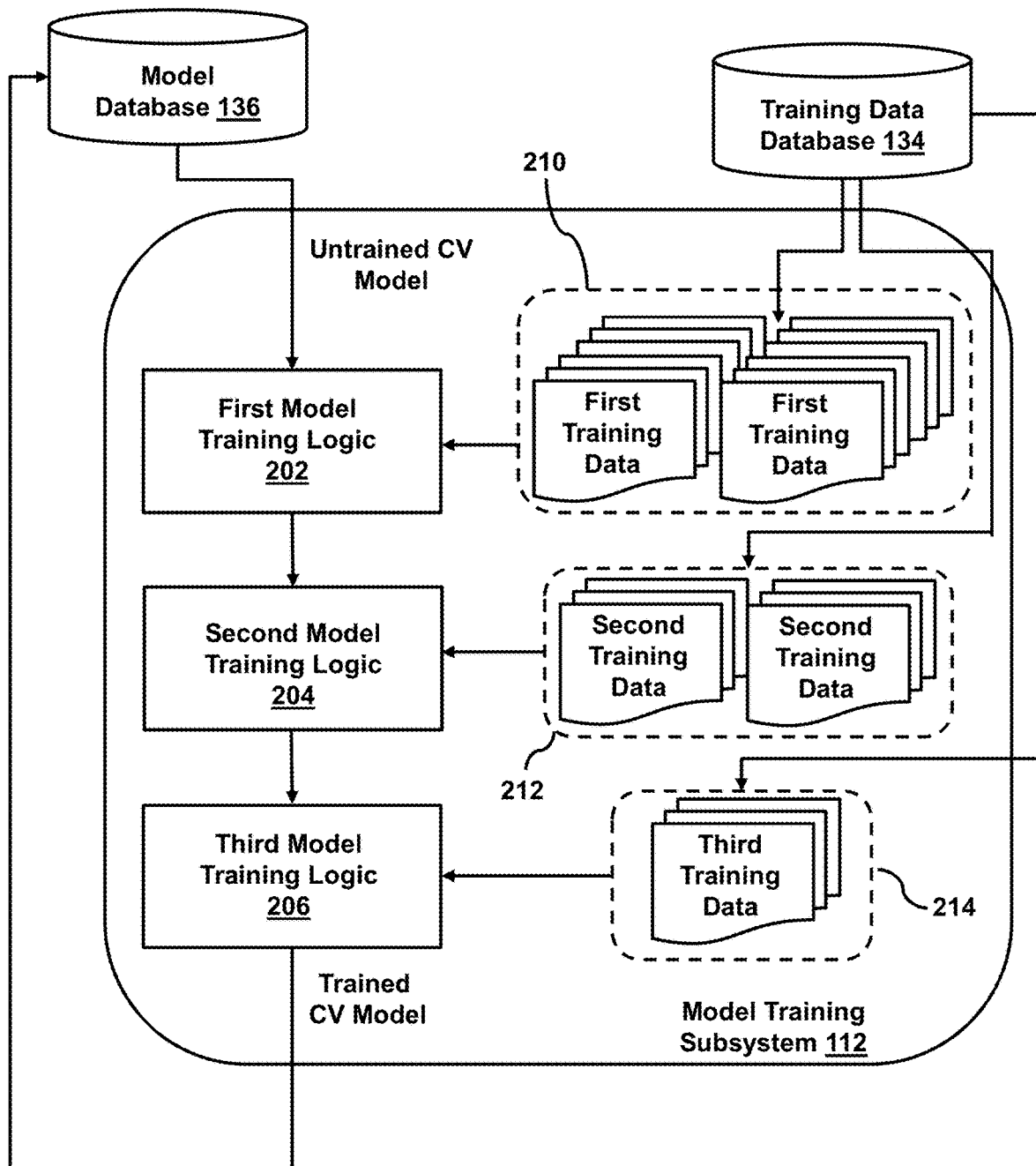
FIGS. 2A and 2B illustrates an example model training subsystem and example training data used to training a computer vision model, respectively, in accordance with various embodiments.

In some embodiments, model training subsystem 112 is configured to train a machine learning model, retrain a previously trained machine learning model, update a machine learning model, update training data used to train a machine learning model, perform other tasks, or combinations thereof. As an example, with reference to FIG. 2A, a training environment may be established by model training subsystem 112 to train (or re-train) a machine learning model to predict whether a patient suffers from a particular medical condition based on an image depicting an anatomical portion of a human captured by wearable device 120 or another image capturing device. In some embodiments, the machine learning model may be trained to detect retinal abnormalities of a patient's retina based on an image depicting the patient's retina. Detection of a particular retinal abnormality may indicate whether the patient suffers from a medical condition. Some example medication conditions include certain ocular diseases, such as diabetic retinopathy, glaucoma, age-related macular degeneration, or other ocular diseases, or combinations thereof.

In some embodiments, model training subsystem 112 may select an untrained machine learning model from model database 136. Alternatively, model training subsystem 112 may select a previously trained machine learning model from model database 136. The type of machine learning model that is selected may be based on a type of prediction to be performed. In some embodiments, the selected machine learning model may include an ensemble of machine learning models each configured to perform a certain set of tasks that feed into one another for generating a predicted result. For example, model database 136 may include various machine learning models that may be selected by model training subsystem 112 to be trained. The various machine learning models stored by model database 136, include, but are not limited to (which is not to suggest that any other list is limiting), any of the following: Ordinary Least Squares Regression (OLSR), Linear Regression, Logistic Regression, Stepwise Regression, Multivariate Adaptive Regression Splines (MARS), Locally Estimated Scatterplot Smoothing (LOESS), Instance-based Algorithms, k-Nearest Neighbor (KNN), Learning Vector Quantization (LVQ), Self-Organizing Map (SOM), Locally Weighted Learning (LWL), Regularization Algorithms, Ridge Regression, Least Absolute Shrinkage and Selection Operator (LASSO), Elastic Net, Least-Angle Regression (LARS), Decision Tree Algorithms, Classification and Regression Tree (CART), Iterative Dichotomizer 3 (ID3), C4.5 and C5.0 (different versions of a powerful approach), Chi-squared Automatic Interaction Detection (CHAID), Decision Stump, M5, Conditional Decision Trees, Naive Bayes, Gaussian Naive Bayes, Causality Networks (CN), Multinomial Naive Bayes, Averaged One-Dependence Estimators (AODE), Bayesian Belief Network (BBN), Bayesian Network (BN), k-Means, k-Medians, K-cluster, Expectation Maximization (EM), Hierarchical Clustering, Association Rule Learning Algorithms, A-priori algorithm, Eclat algorithm, Artificial Neural Network Algorithms, Perceptron, Back-Propagation, Hopfield Network, Radial Basis Function Network (RBFN), Deep Learning Algorithms, Deep Boltzmann Machine (DBM), Deep Belief Networks (DBN), Convolutional Neural Network (CNN), Deep Metric Learning, Stacked Auto-Encoders, Dimensionality Reduction Algorithms, Principal Component Analysis (PCA), Principal Component Regression (PCR), Partial Least Squares Regression (PLSR), Collaborative Filtering (CF), Latent Affinity Matching (LAM), Cerebri Value Computation (CVC), Multidimensional Scaling (MDS), Projection Pursuit, Linear Discriminant Analysis (LDA), Mixture Discriminant Analysis (MDA), Quadratic Discriminant Analysis (QDA), Flexible Discriminant Analysis (FDA), Ensemble Algorithms, Boosting, Bootstrapped Aggregation (Bagging), AdaBoost, Stacked Generalization (blending), Gradient Boosting Machines (GBM), Gradient Boosted Regression Trees (GBRT), Random Forest, Computational intelligence (evolutionary algorithms, etc.), Computer Vision (CV), Natural Language Processing (NLP), Recommender Systems, Reinforcement Learning, Graphical Models, or separable convolutions (e.g., depth-separable convolutions, spatial separable convolutions, etc.).

In some embodiments, the selected model or models may include a computer vision model. Model training subsystem 112 may retrieve the selected computer vision model, which may be untrained or require additional training (e.g., such as retraining on new or updated training data), from model database 136, and pass the selected model to first model training logic 202. In some embodiments, model training subsystem 112 includes first model training logic 202, second model training logic 204, and third model training logic 206. Each of logics 202-206 represents a stage of the training process for the selected model. Various stages of training may be included to refine the model to detect particular objects within particular types of images. For instance, some embodiments include a trained machine learning model configured to detect ocular diseases within images. Some embodiments may include a trained machine learning model configured to detect ocular diseases within infrared or near infrared images by identifying whether the infrared image includes an instance of one or more retinal abnormalities. Retinal issues to be detected may include vascular etiologies, such as small dot hemorrhages, microaneurysms, and exudates.

In some embodiments, the number of available infrared images for use in training a machine learning model to detect one or more specified ocular diseases may be limited. For example, a number of infrared images labeled as depicting healthy or unhealthy retina may be less than 100,000 images, less than 10,000 images, less than 1,000 images, etc. The limited quantity of labeled infrared images can prevent the machine learning model from being accurately trained (e.g., an accuracy of the trained model being less than a threshold accuracy). In some embodiments, the selected machine learning model may be trained using transfer learning techniques. For instance, the selected machine learning model may be initially trained using a large corpus of data differing from the target data that the final model is to be used for. The initial stage of training may serve to obtain weights and biases for lower layers of machine learning models, while later stages of the training process may use more task-specific data to refine and determine weights and biases for upper layers of the machine learning models, however the weights and biases of the lower layers are not precluded from being adjusted during the later stages of the training process based on the additional data.

Model training subsystem 112 may obtain various data sets from training data database 134 to be used during the various training stages. For instance, a corpus of images 210 may be retrieved and used as first training data for performing a first stage of model training, a set of images 212 may be retrieved and used as second training data for performing a second stage of model training, and a set of infrared images 214 may be retrieved and used as third training data for performing a third stage of model training. In some embodiments, corpus of images 210 may include more than 1 million images, more than 10 million images, more than 100 million images, or more. Each image from corpus of images 210 may include one or more labels each indicating a category of an object that the respective image depicts. For example, an image from corpus of images 210 may include a label indicating that the image depicts a dog or a cat. Each label represents a category from a plurality of categories with which images included within corpus of images 210 has been pre-classified. For example, corpus of images 210 may represent images classified into at least one of 1,000 or more categories, 10,000 or more categories, 20,000 or more categories, or more. Using corpus of images 210, first model training logic 202 may train the "to-be-trained" computer vision model to obtain a first trained computer vision model. At this stage of the training process, the first trained computer vision model may be capable of detecting whether a given image input to the model depicts an object, and a most likely classification of that object based on the plurality of categories of corpus of images 210. For example, the first trained computer vision model may output, in response to the input image, a classification vector having N-dimensions, where N represents the number of categories represented by corpus of images 210. Each dimension of the classification vector refers to one of the plurality of categories. The classification vector stores a classification score for each category, where the classification score represents how likely the first trained computer vision model determined that the input image depicts that category's object (e.g., does the input depict a cat or dog?). In some embodiments, the first trained computer vision model may output a result indicating the most likely object depicted by the input image based on the classification scores included within the classification vector. For example, if the classification score for the "dog" category is 0.7 and the classification score for the "cat" category is 0.3, then the model may determine that the input image depicts a dog.

As mentioned previously, an end goal of model training subsystem 112 may be train a computer vision model to detect ocular diseases within infrared images. However, due to limitations of available training data for images depicting ocular diseases (including images that do not depict any disease), as well as infrared images depicting ocular diseases (including infrared images that do not depict any ocular diseases), model training subsystem 112 may employ a first training stage where lower layer weights and biases (as well as higher layer weights and biases) may be coarsely trained on a large dataset of images depicting objects unrelated to ocular diseases. During a second training stage, the first trained computer vision model may be trained again using a smaller, more specific, set of images.

In some embodiments, second model training logic 204 may be configured to perform a second training to the first trained computer vision model using a set of images 212. Set of images 212 may be used as second training data to train the first trained computer vision model (e.g., the model trained during the first training step via first model training logic 202). Set of images 212 may include fewer images than that of corpus of images 210. For example, set of images 212 may includes less than 1 million images, less than 100,000 images, less than 10,000 images, or less. Each image included within set of images 212 may be an image of a human retina including a retinal abnormality or without a retinal abnormality. In some embodiments, a retinal abnormality refers to one or more properties, characteristics, or traits present in an image of a retina that are found when a person has a particular ocular disease. In some embodiments, images within set of images 212 include one or more labels indicating a category that a respective image has been classified into. Set of images 212 may include M-categories, and each category represents a particular retinal abnormality or ocular disease depicted by the images in that category. For example, images in set of images 212 labeled as depicting retinas having diabetic retinopathy will depict retina including one or more retinal abnormalities consistent with diabetic retinopathy. Some example retinal image databases which may be used to populate set of images 212 include, but are not limited to, (which is not to imply that other lists are limited), Retinal Identification Database (RIDB), Retinal Images vessel Tree Extraction (RITE), High-Resolution Fundus (HRF) Image Database, Retinal Fundus Multi-Disease Image Dataset (RFMID), or other databases, or combinations thereof. Using set of images 212, second model training logic 204 may train the first trained computer vision model to obtain a second trained computer vision model. At this stage of the training process, the second trained computer vision model may be capable of detecting whether a given image input to the model depicts a retina including one or more retinal abnormalities or an ocular disease, and a most likely classification of that object based on the categories of set of images 212. For example, the second trained computer vision model may output, in response to the input image, a classification vector having M-dimensions, where M represents the number of categories represented by set of images 212, and M is less than N (e.g., the number of dimensions of the classification vector output by first trained computer vision model).

In some embodiments, the second trained computer vision model may be provided to third model training logic 206 to perform a third training step. Third model training logic 206 may be configured to perform a third training to the second trained computer vision model using a set of infrared images 214. Set of infrared images 214 may be used as third training data to train the second trained computer vision model (e.g., the model trained during the second training step via second model training logic 204). Set of infrared images 214 may include fewer images than that of set of images 212. For example, set of infrared images 214 may include less than 100,000 infrared images, less than 10,000 infrared images, less than 1,000 infrared images, or less. Each infrared image included within set of infrared images 214 may be an infrared image of a human retina including a retinal abnormality or without a retinal abnormality. Similar to set of images 212, each infrared image within set of images 212 may include one or more labels indicating a category that a respective infrared image has been classified into. Set of infrared images 214 may include P-categories, and each category represents a particular retinal abnormality or ocular disease depicted by the images in that category. Some cases include set of infrared images 214 having a different number of categories than set of images 212. For instance, set of infrared images 214 may include fewer categories than set of images 212. This may be due to the number of retinal abnormalities that can be detected from infrared images as opposed to images captured using visible light. For example, infrared images in set of infrared images 214 labeled as depicting retinas having diabetic retinopathy will depict retina including one or more retinal abnormalities consistent with diabetic retinopathy. Differing, though, from set of images 212, set of infrared images 214 may include infrared images depicting a retina. An infrared image refers to an image captured using an infrared imaging component or other image sensor that captures the infrared image (and in some cases, other frequencies) based on infrared light output by an infrared light source that reflects off a rear inner surface of the eye. Additional details regarding the infrared image capturing component are included below with reference to FIGS. 3, 4A, and 4B. The infrared images may not be visible to a human, but may be used as input by a computer. For example, each infrared image may be stored as an array of pixel values, where each pixel value represents an intensity of infrared light incident on the pixel's sensor.

Using set of infrared images 214, third model training logic 206 may train the second trained computer vision model to obtain a trained computer vision model. At this stage of the training process, the trained computer vision model may be capable of detecting whether a given infrared image input to the model depicts a retina including one or more retinal abnormalities or an ocular disease, and a most likely classification of that object based on the categories of set of infrared images 214. For example, the trained computer vision model may output, in response to the input infrared image, a classification vector having P-dimensions, where P represents the number of categories represented by set of infrared images 214, and P may be less than or equal to M (e.g., the number of dimensions of the classification vector output by the second trained computer vision model) and less than N (e.g., the number of dimensions of the classification vector output by first trained computer vision model).

Figure 2B:
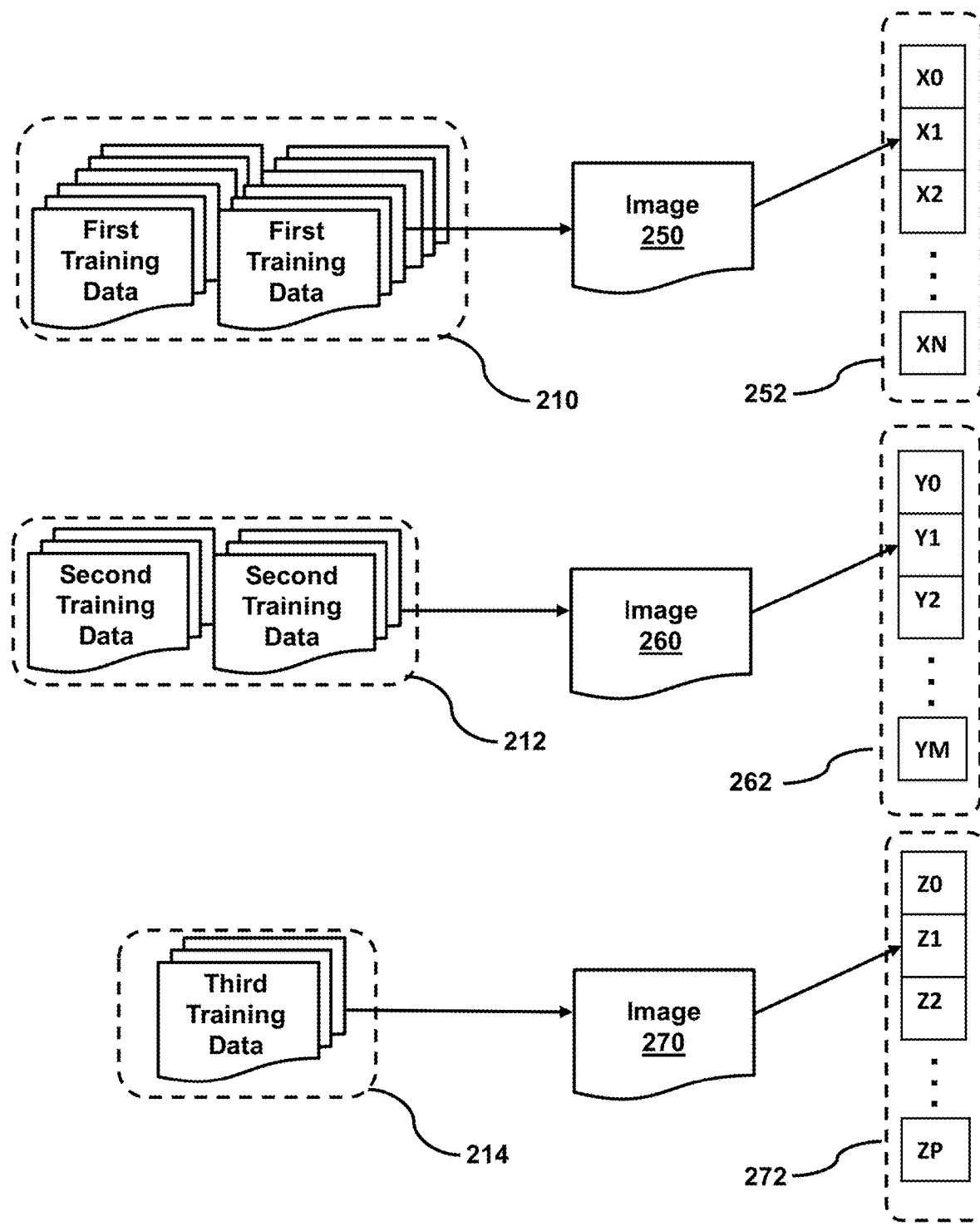

As shown with respect to FIG. 2B, each image included within corpus of images 210 may be pre-classified into one or more of categories 252. For example, image 250 represents an image from corpus of images 210. Image 250 may include a label Xl, which refers to a first category of categories 252 (e.g., N categories). If image 250, or an image that is substantially similar to image 250 (e.g., including different contrast levels, greyscale, cropped, etc.) were to be input into a computer vision model trained using corpus of images 210, then image 250 would be expected to be classified into the first category of categories 252. Similarly, each image included within set of images 212 may be pre-classified into one or more of categories 262. For example, image 260 represents an image from set of images 212. Image 260 may include a label Yl, which refers to a first category of categories 262 (e.g., M categories). If image 260, or an image that is substantially similar to image 260 (e.g., including different contrast levels, greyscale, cropped, etc.) were to be input into a computer vision model trained using set of images 212 (e.g., as well as corpus of images 210), then image 260 would be expected to be classified into the first category of categories 262. Each infrared image included within set of infrared images 214 may be pre-classified into one or more of categories 272. For example, image 270 represents an image from set of infrared images 214. Image 270 may include a label Z1, which refers to a first category of categories 272 (e.g., P categories). If image 270, or an image that is substantially similar to image 270 (e.g., including light of a different infrared wavelength) were to be input into a computer vision model trained using set of infrared images 214 (e.g., as well as corpus of images 210, set of images 212), then image 270 would be expected to be classified into the first category of categories 272.

In some embodiments, the computer vision model may be a transformer network for images, which can also be referred to as a visual transformer. An example visual transformer is ViT. In some embodiments, transformers (specifically, Visual Transformers) may be used to analyze and classify images. Transformers are a self-attention-based architecture often used for Natural Language Processing (NLP), and have been shown to perform well for NLP tasks. The input for these transformers is tokens (e.g., which, for NLP-related tasks, include n-grams) that come with a classifier. The attention model mechanisms introduce weights to the words based on the importance of each word. The goal of the attention model is to determine which words are strongly weighted with the context and relationship of a current word in the analysis. The model attempts to focus on the relevant information and provide the relevant information as a signal to a network. To do this, the transformer includes an encoder that uses a scaled-dot product attention to determine the focus from a vector of scores that indicate importance. The transformer may use an encoder to take an input and transforms the input into an embedding. A decoder may be used for producing an output. Using a scaled dot product function, a transformers can generate scores that have multiple (e.g., three) learnable weight layers. These weight layers are applied to the encoded input, and the outputs are called key, query, and value. The computed scores can be input to the Softmax function to calculate a final attention embedding. Thus, the embedding vectors can encode both the position of a word and a distances between words. A benefit of transformers is that transformers do not need to process sequential data in order. This allows for transformers to be parallelized, and thus transformers scale well even as input sequence length increases.

Visual transformers, such as ViT, act similarly to transformers used for natural language processing, albeit for images. Visual transformers can be used for computer vision problems involving image classification, object detection, and semantic image segmentation, using, for example, self-attention to aggregate information. Visual transformers may split an image into patches and provide a sequence of linear embeddings of the patches as input. The image patches are treated the same as tokens used for natural language processing, and the model is trained (supervised) on image classification. Like transformers, visual transformers may add a classification token to the sequence. While an NLP transformer receives a 1D input, visual transformers are configured to handle 2D (or 3D) images. To do this, an image is split into fixed-size patches, which also serves as the effective input sequence length for the transformer, linearly embed each patch, add position embeddings, and feed to the resulting sequence of vectors to an encoder. The patches may be flattened and mapped to the dimensions of the latent vector with a trainable linear projection. The output of the trainable linear projection are the patch embeddings. Some cases include visual transformers using a constant latent vector size throughout all layers.

A learnable embedding is prepended to a sequence of embedded patches. The state of the embedded patches at the output of the transformer encoder serves as the image representation. A classification head is attached to the transformer encoder during the pre-training and fine-tuning, and may be implemented by a multi-layer perceptron layer (MLP), which includes one hidden layer at pre-training. A single layer can implement the classification head during the fine-tuning stage.

To retain positional information, position embeddings may be added to patch embeddings, and the resulting embedding vectors can be input to the encoder. The encoder may include a multi-head self-attention (MSP) layer, a multi-layer perceptron's (MLP) layer, and a layer norm (LN). The MSP layer concatenates all the attention outputs linearly to the right dimensions. The many attention heads help train local and global dependencies in an image. The MLP layer may include two-layer with Gaussian Error Linear Unit. The LN may be added prior to each block as it does not include any new dependencies between the training images. Residual connections may be applied after every block to improve the training time and overall performance.

Visual transformers may be pre-trained on large datasets and fine-tuned to smaller downstream tasks. For example, visual transformers may perform multiple stages of training, where in a first stage the visual transformer is trained on a first dataset, and during a second stage (or subsequent stages), the "trained" model is trained on a smaller dataset. The first layer of a visual transform can linearly project flattened patches into a lower-dimensional space. A learned position embedding may then be added to the patch representations after the embedding. The model learns to encode distance within the image in the similarity of position embeddings. That is, closer patches tend to have similar position embeddings.

The self-attention layer may include multiple self-attention heads and has a mix of local heads and global heads (with small and large distances, respectively). In lower layers, some heads attend to most of the image. Incorporating local information at lower layers may be achieved by early attention layers via performance of large scale pre-training (e.g., first training stage), thereby allowing the model to integrate information globally. The model attends to image regions that are semantically relevant for classification.

In some embodiments, multi-layer perceptron-based architecture (MLP-Mixer) may be used to analyze and classify the images. An MLP-Mixer is based on a multi-layer perceptron (MLP). The MLP-Mixer does not use convolutions or self-attention. Instead, MLPs are repeatedly applied across either feature channels or spatial locations. They rely on basic matrix multiplications, scalar non-linearities, and changes to data layout, such as transpositions and reshapes. The MLP-Mixer accepts a sequence of linearly project image patches (tokens) shaped as a table and maintains the dimensionality of the table throughout. Two types of MLPs can be used in the MLP-Mixer: a channel-mixing MLP and a token-mixing MLP. The channel-mixing MLP allows communication between different channel and operates on each token independently, taking individual rows of the table as input. The token-mixing MLP allows communication between the different spatial locations, or tokens. They operate on the individual channels independently, taking the individual columns of the table input. The MLP-Mixer can separate the channel-mixing (per location) operations and the token-mixing (cross-location) operations. The MLP-Mixer takes a sequence of non-overlapping image patches as input with each patch being projected into a hidden dimension. The result is a 2D real-value input table. The number of patches is determined based on the resolution of the original input image and the resolution of each patch, where the patches are linearly projected using a projection matrix that is the same for all patches. MLP-Mixer layers may include multiple layers, each having the same size and formed of two MLP blocks. The first block is the token-mixing block which acts on the columns of the real-valued table and is shared across all columns so the same MLP is applied to each of the different features. The second block is the channel-mixing block which acts on the rows of the real-valued table and is shared across all columns. Every MLP block may include two layers that are fully connected and a non-linearity (e.g., ReLu) that is applied to each row of its input data tensor independently.

Each layer, except for the initial patch projection layer, may take an input of the same size. Aside from the MLP layers, the MLP-Mixer may use skip connections and layer normalization. However, MLP-Mixers do not use position embedding due to the token-mixing MLPs being sensitive to the order of the input tokens. The MLP-Mixer also can use a standard classification head with the global average pooling (GAP) layer followed by a linear classifier.

Figure 3:
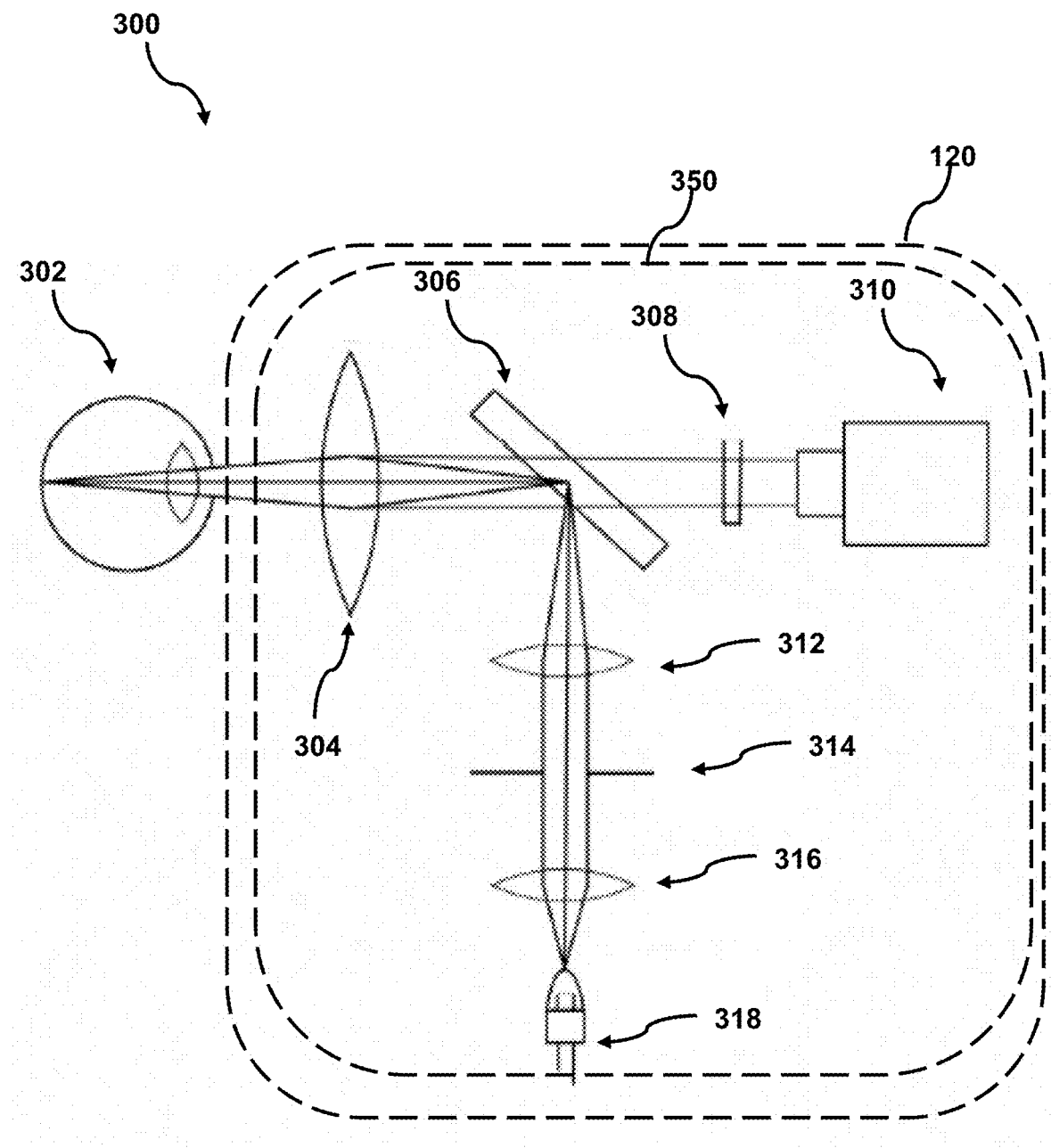
FIG. 3 illustrates an example optical pathway formed by a patient adorning a wearable device, in accordance with various embodiments.

FIG. 3 illustrates an example optical ray pathway 300 formed by a patient adorning a wearable device, in accordance with various embodiments. In FIG. 3, optical ray pathway 300, (e.g., including through a headset to a camera, may include an eye 302 of a patient. While the techniques described herein refer to detecting retinal abnormalities in a retina, retinal abnormalities may be detected in either eye of the patient. This may be performed by obtain an image of both eye's or obtaining two images, one of either eye. However, to avoid obfuscating aspects of optical ray pathway 300, only a single instance of eye 302 is depicted. As seen from FIG. 3, a portion of optical ray pathway 300 may be formed within wearable device 120, as described below. Wearable device 120 may be worn by a patient and oriented about the patient's face such that a camera unit 310 is aligned with a center of a patient pupil. Optical ray pathway 300 may include a convex lens 304 (e.g., which may include multiple lenses packaged together to focus light in a particular manner). In some embodiments, wearable device 120 includes an optical processing unit 350 configured to focus light output from an illumination unit 318, and capture images of eye 302 based on the light reflecting off portions (e.g., a rear inner surface) of eye 302. Optical processing unit 350 may include convex lens 304 and a beam-splitter 306, which guides the incident and backscattered light to and from the patient's retina. Optical processing unit 350 may also include a light polarization filter 308 and infrared imaging component 310 that captures en face images of eye 302 (e.g., the retina). Optical processing unit 350 may further include convex lenses 312 and 316, and an aperture 314 that controls a size and shape of an area of the retina to be illuminated.

In some embodiments, the incident light rays may originate from a location coaxial with infrared imaging component 310 that ultimately captures the (infrared, non-infrared) images of the retina. In some embodiments, the light may originate from a location perpendicular to the camera-patient eye axis and be guided towards the patient's eye using a beam-splitter (e.g., beam-splitter 306). The incident light may be passed through aperture (e.g., aperture 314), which may be an adjustable aperture, with a given size and shape to control and alter the area of the retina to be illuminated.

Figure 4A:
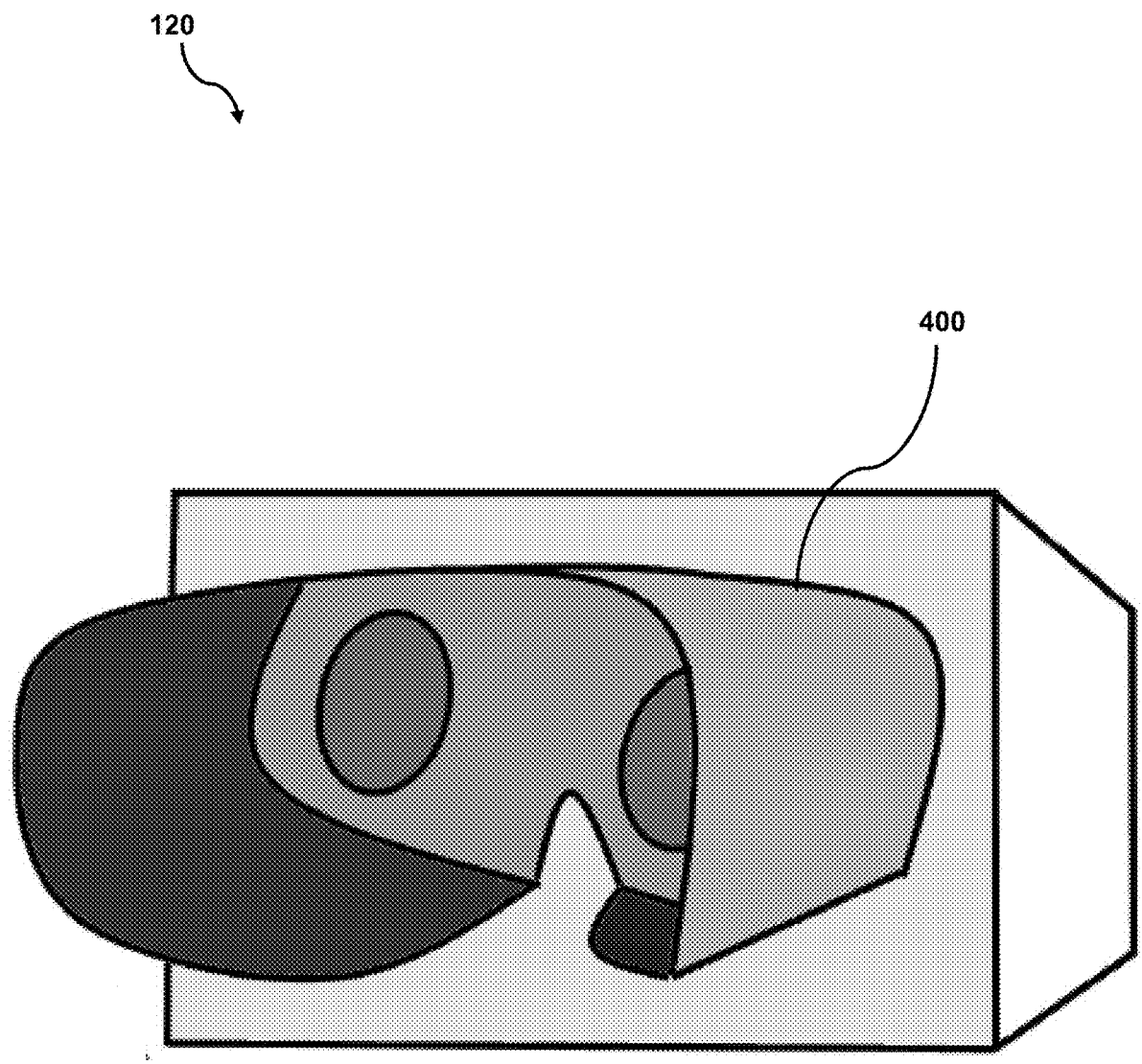
FIGS. 4A-4C illustrate an example perspective view and block diagram of a wearable device, in accordance with various embodiments.
Figure 4B:
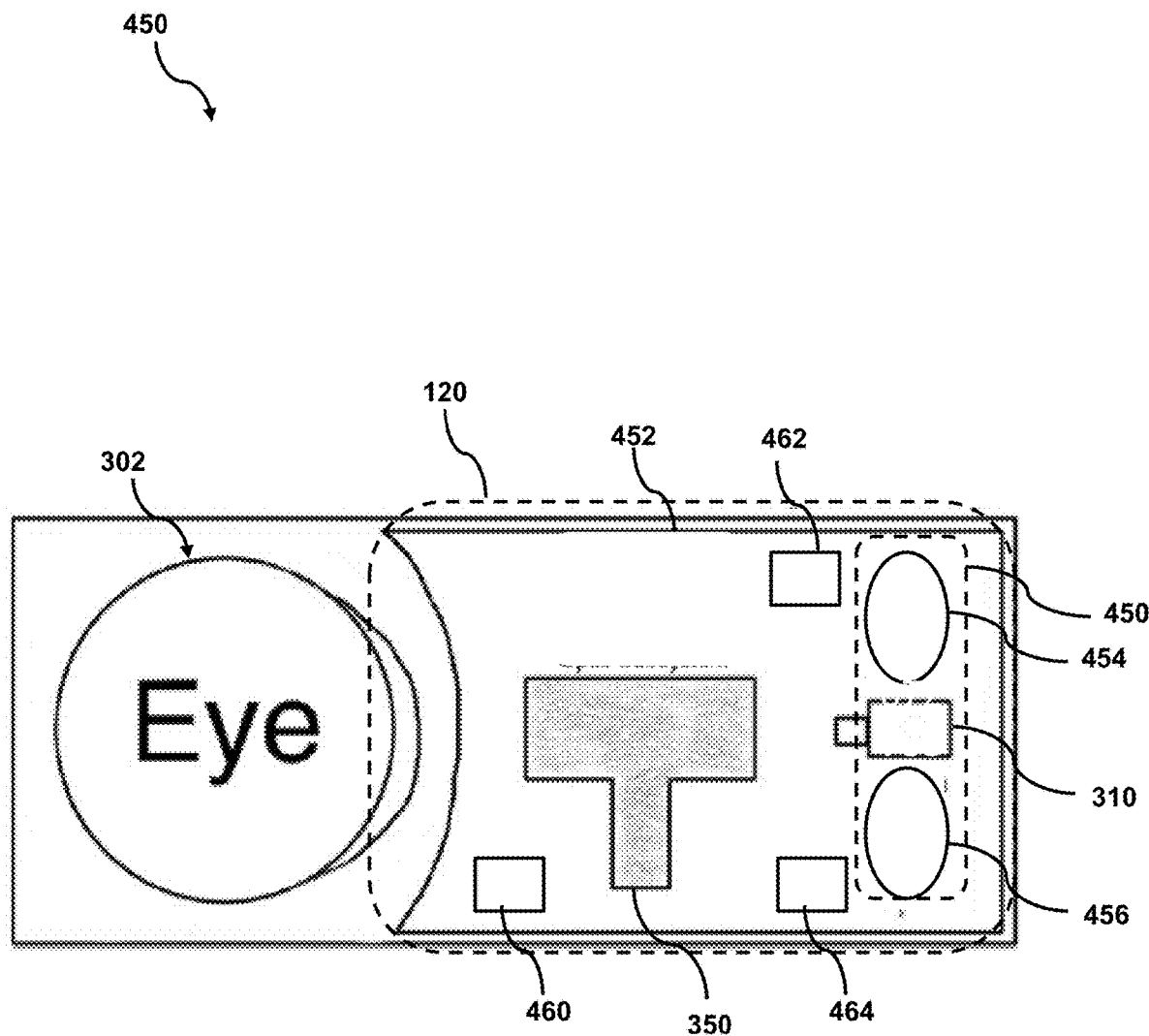

FIGS. 4A and 4B illustrate an example perspective view and block diagram of a wearable device, in accordance with various embodiments. As seen in FIG. 4A, wearable device 120 may include, or form a part of, a retina imaging system. Wearable device 120 may include a headset (e.g., a portion to affix, when worn, to a head of a patient) and an eye cuff 400 (Ambient Light Protective Gear). The headset may be used to package all system components into a user-friendly device. In addition to housing the optical and illumination system, the headset and eye cuff may also interface with the patient in a such a way to eliminate or reduce ambient light from entering a volume formed by the negative space between the patient's face and inner surfaces of wearable device 120. (e.g., enclosing some or all of the patient's eyes, lenses, light source, or camera). Light leaks could prevent the patient's pupils from relaxing, which then severely limits the functionality of illumination unit 318, particularly when capturing IR images.

Eye cuff 400 may prevent light leaks into the volume defined by wearable device 120. In some embodiments, eye cuff 400 may be a compressible molded eye cuff designed to fit a wide range of human faces. Another embodiment of the eye cuff may have modular eye cuffs which can be swapped for best fit with the patient. The eye cuff may be constructed from a compressible, malleable material which does not become brittle upon deformation, such as silicone, compressed polyester, or a polyurethane foam, so that the cuff can be pressed to conformally fit different patient faces. In some embodiments, when pressed to a face, the face and the eye cuff may define a darkened volume. Portions of the headset adjacent that volume may be coated with a light-absorbing material. A photoresistor- or photodiode-based light sensor may be placed within the headset to monitor possible light leakage due to improper sealing, or in some cases, the camera of a smartphone may be used, e.g., prior to IR illumination. In some embodiments, in response to detecting light having an intensity greater than an ambient light leak threshold, the ambient light sensor may output a signal to client device 140, wearable device 120, both, or components thereof, of the presence of a light leak to prevent capture of any images. For example, the light sensor may send a signal to infrared imaging component 310 to prevent images from being captured. In some embodiments, the light sensor may also be configured to output a signal to cause an alert to be displayed to the patient or a medical provider. For example, the signal may cause a particular alert message or graphic to be displayed to the patient via a display (e.g., a heads-up display) included by wearable device 120, a display of client device 140, other displays, or other components of system 100, or combinations thereof.

Figure 4C:
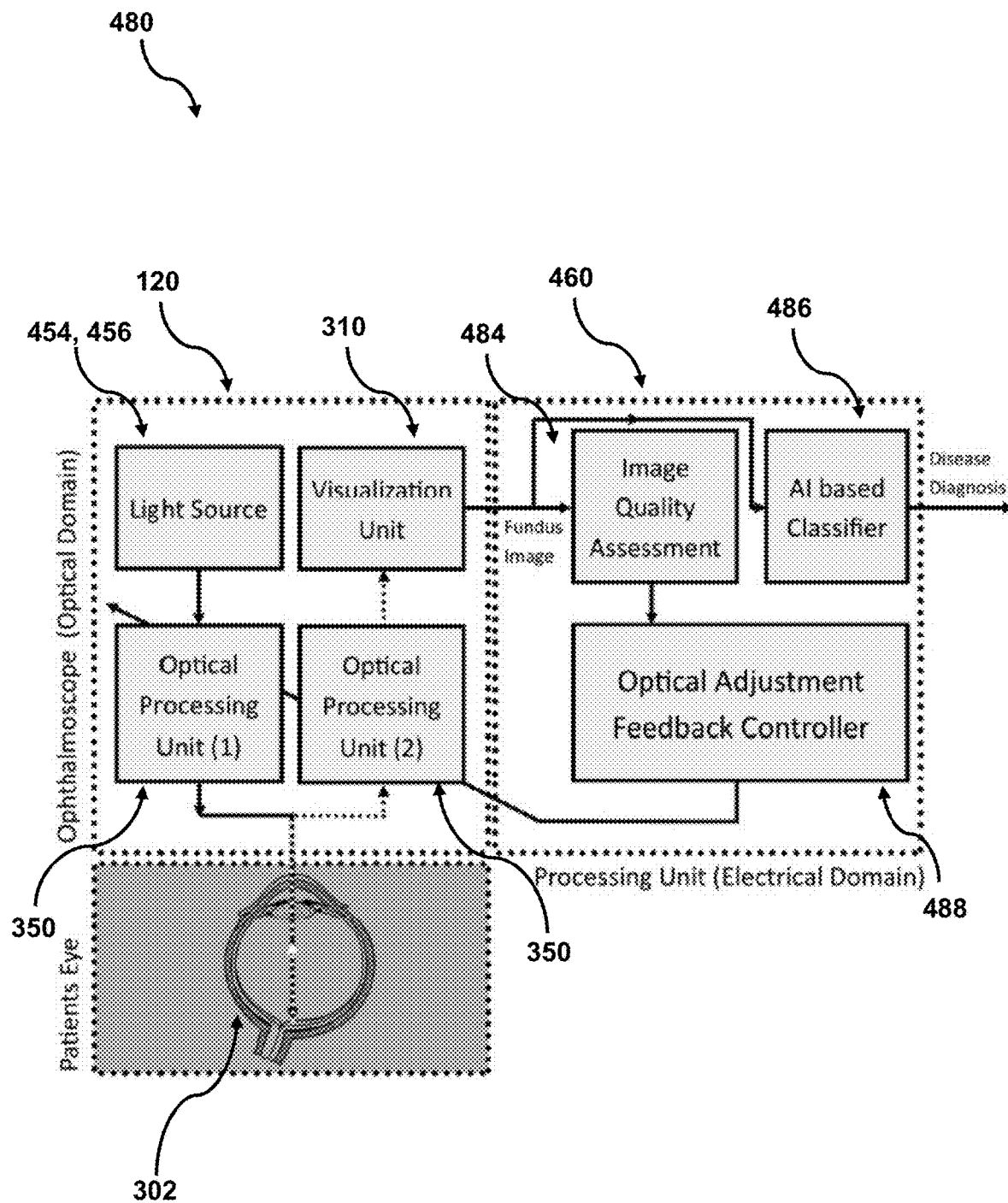

FIGS. 4B and 4C depicts a block diagrams of wearable device 120. While certain features are illustrated in only one of FIGS. 4B and 4C, this is done merely to prevent obfuscation of the figures and does not imply that any depiction of wearable device 120 must be wholly described by one of FIGS. 4B and 4C. In some embodiments, a retina imaging system may include an image detection system 452, and image detection system 452 may include optical processing unit 350. Backscattered light from a patient's eye may be altered using optical processing unit 350. Optical processing unit 350 may include one or multiple convex or concave (refractive) lenses to correct for the patient's myopia or hyperopia and to focus the light reflected from the patients retina on an image plane across an infrared imaging component 310 (e.g., a camera). The lenses can be put in particular configurations to magnify the imaging view from the patients retina. For example, a proposed configuration of optical processing unit 350 (a convex lens in this case) is shown in FIG. 3 (304, 306, 312-316). In some cases, positions of lenses can be adjusted using optical adjustment feedback controller 488. Optical adjustment feedback controller 488 may be include, for example, dials on accessible by a patient on wearable device 120, which may be mechanically coupled to threaded actuators 462, 464 that causes wearable device 120 to translate further or closer to one another, or automatically via actuators 462, 464 coupled to a motor.

In some embodiments, optical processing unit 350 may include a polarization system. The illuminated light may be unwantedly reflected from the surfaces of optical processing parts and other parts of the enclosure that are present in the system. For example, light can be reflected from the surface of the lenses and create glare or artifacts in the final images produced. Such an effect can be eliminated or reduced by differentiating the polarization of the light that is backscattered from the patient's retina and the light that comes out of a light source (e.g., illumination unit 318). An example of this polarization concept is shown in FIG. 3 (e.g., infrared imaging component 310).

In some embodiments, wearable device 120 may include an image detection system 452 that includes a camera system 450. Camera system 450 may include an infrared light source 454 and an infrared imaging component 310. Infrared imaging component 310 may be configured to capture infrared images based on infrared light output by infrared light source 454. Thus, as described herein, infrared imaging component 310 may be referred to interchangeably as an imaging component. In some embodiments, camera system 450 may also include a visible light source 456. In some cases, where camera system 450 also includes visible light source 456, imaging component may also function to capture images using visible light, and thus can be referred to herein interchangeably as a visible imaging component. In some cases, image detection system 452 or camera system 450 may include a separate visible imaging component. In other words, imaging component 310 may be configured to capture infrared images and images in the visible spectrum. Infrared imaging component 310 may be an IR camera, and may be used to capture the backscattered IR light from the patient's retina. In some embodiments, IR cameras are materialized by removing the IR filter that blocks IR light from triggering the sensing network that exists in cameras optimized for the visual spectrum that is primarily sensitive to the visible range of the electromagnetic spectrum (400 nm-700 nm).

A focusing lens can be directly mounted on to a sensing aperture of imaging component 310. The intention for this focusing lens is to properly converge the backscattered light, e.g., IR light, from the patient's retina onto the sensing matrix of imaging component 310. A system of additional external lenses can also be used to further process the backscattered IR light from the patient's retina. This further processing can be done with the aim of image enhancement and or magnification. An embodiment of such external lenses is shown FIG. 3 (e.g., convex lens 304). In some cases, the device may have a plurality of cameras with different focal lengths and spatial positions. Some embodiments may replicate components in the headset to facilitate imaging with these various cameras, e.g., concurrently or serially, in some cases with varying exposure times to expand operate beyond the dynamic range of the image sensor. In some cases, these images may be combined with computational photography techniques.

The goal of using the IR cameras is to get focused enface fundus images. The IR light rays are generally invisible to the human eye. Hence, the patient's eye pupil would not contract when exposed to IR light. This is particularly very useful to get a wider view of the retina. It has been well studied that it is not possible to capture pathologically meaningful images of the fundus if the patient's pupil is contracted. The ambient light protective gear, mentioned above, helps achieve a wider patient eye pupil due to the dilation that naturally occurs in darkness.

In some embodiments, infrared light may be used to illuminate the fundus without contracting the pupil. Using convex lenses, the backscattered IR light may be processed so that a focused view of the retina is obtained. Once such an image is captured, visible light source 456 may be turned on and project light in the visible range and, instantaneously (e.g., within less than 500 ms, such as less than 100 ms or within 10 ms), capture a focused image of the retina that is illuminated using visible light. It should be noted that the IR light and the visible light have the same properties and undergo the same changes when interacting with optical processing unit 350 such as the lenses. That is why the properties of optical processing unit 350, such as the lens strengths and location, may not be altered in some embodiments for the visible light if a focused light with the IR illumination was obtained. It is also worth mentioning that, in some embodiments, the visible light illumination and image acquisition takes place instantaneously (e.g., within less than 500 ms, like less than 100 ms, such as within 10 ms) such that the patient's eye pupil does not have a time to contract and limit the field of view. For example, one or more processors included by optical processing unit 350 may be configured to detect that the visible light output signal, and may generate a trigger signal to cause the visible image acquisition (e.g., via imaging component 310) to occur.

Some embodiments may use multiple wavelengths of visible, infrared, or visible and infrared light. The utilization of a continuous spectrum of visible light (white light) to illuminate the retina and capture fundus images is optional, which is not to suggest that other described features are required. In fact, the IR imaging mechanism may be sufficient for all practical pathological purposes. In other embodiments, multiple discrete illumination wavelengths may be used and capture fundus images sequentially or in parallel. Different tissue cells in the retina exhibit different reflective properties when illuminated with light rays of different wavelengths. As such, different wavelengths can capture different pieces of information about the pathologies of the retina. It should be noted that if a wavelength in the visible range is used, the image acquisition should happen instantaneously in some embodiments to avoid (or reduce the amount of) the patient's eye pupil contraction.

In some embodiments, the retina imaging system may include processing unit 460. In some embodiments, the fundus' optical signals are captured by imaging component 310, and converted to an electrical signal received by processing unit 460. In some embodiments, processing unit 460 may be part of another computing system, such as computing system 102, client device 140, or both. In some embodiments, processing unit 460 can be physically materialized in the same package that contains the illumination and the optical processing units (e.g., wearable device 120). In another embodiments, the captured electrical signals can be uploaded to the cloud. A remote processing unit may then classify the images and makes the patient recommendations.

In some embodiments, processing unit 460 may further be configured to perform various on-device image processing steps to filter images, enhance images, apply filters to images, screen images for instances of particular retinal contraindicators (e.g., a patient with cataracts would be unable to have their fundus imaged). For example, processing unit 460 may be configured to obtain an initial image or set of images of eye 302, and determine whether eye 302 is capable of being used to capture infrared images of the patient's retina. In some cases, processing unit 460 may operate a binary classifier configured to determine whether the patient's retina can be imaged. Certain ocular conditions can prevent images of the retina from being captured. For example, a patient suffering from cataracts would not be able to have their retina imaged. Therefore, the binary classifier implemented by processing unit 460 may serve as an initial check of whether additional processes can be performed, such as capturing images of the retina and determining whether the retina includes any retinal abnormalities. In some embodiments, the binary classifier implemented by processing unit may take an initial image or images in the visible or IR spectrum, and determine whether certain optical landmarks are present. For example, the binary classifier may detect whether a particular optical vein or other optical feature is present within the captured image, and classify that image is containing or not containing the desired optical feature. If the optical feature is not present in the captured images, then this indicates that the patient's eye (e.g., eye 302) will not be able to be used to detect retinal abnormalities. In such cases, a signal or alert may be provided to the patient or medical practitioner to indicate that images of the retina are not able to be captured.

Various processing steps may be performed by processing unit 460. In some cases, the code may include computer program instructions to perform these steps. The code may be downloaded to wearable device 120 (e.g., within memory of wearable device 120). In some cases, the code may be downloaded to computing system 102, wearable device 120, client device 140, or combinations thereof (e.g., as a native application or in some cases an application executing server-side may perform the analysis).

The software components of retina screening system 480 may include an image capturing module to capture, process, and output images. In some embodiments, software controls illumination (e.g., infrared light source 454, visible light source 456), vision guidance (e.g., optical adjustment feedback controller 488), imaging component 310, or other components. Some embodiments of the vision guidance may include an indicator LED for the patient to visually follow to calibrate and orient a position of one or more components of wearable device 120, such as infrared light source 454, visible light source 456, imaging component 310, lenses, apertures, polarizers, or other components. In some cases, optical adjustment feedback controller 488 may allow for precise control of hardware included within wearable device 120 to capture high quality images using any or all of the methods described below.

Some embodiments of optical adjustment feedback controller 488 can use a mechanical system to adjust imaging component 310 so that it is coaxial with the patient's eye.

In some embodiments, wearable device 120 may include, below imaging component 310, a small rectangular LED screen which projects a dim green light. By translating the light in the x-direction, some embodiments can direct the patient's gaze to get a panorama-like wide-field image of the retina. This guide may also have a feedback indicator to let the patient know the screening procedure is being followed correctly.

In some embodiments, visible light source 456 may include an LED of a particular color (e.g., green, yellow, red). The LED color (e.g., visible in the dark volume) may be changed from one color to another, to yet another (e.g., from red to yellow to green) to indicate that an eye is not found, the appropriate alignment between imaging component 310 and the user's eye is not yet achieved, and successful alignment, respectively. For instance, optical adjustment feedback controller may cause actuators 462, 464 to adjust a position of imaging component 310, light sources 454, 456, lenses included within optical ray pathway 300, or other components, to align the patient's eye and imaging component 310.

A quality control software module may control for the determination that a usable image has been captured using any or all of the methods below. For instance, order to preserve battery life, infrared light source 454, visible light source 456, or both, may be not enabled until a human face, eye, or other anatomical feature is detected by optical processing unit 350. This computation is accomplished using methods described in Quality Control. In some embodiments, optical processing unit 350 may implement a face classifier or eye classifier, such as those available from the OpenCV library, to detect certain optical features. Optical processing unit 350, for example, may first perform one or more pre-processing steps, such as cropping, rotating, skewing, blurring, gray scaling, and the like, to a captured image (e.g., an initially captured image for use in detecting anatomical features). Optical processing unit 350 may then take the pre-processed images and detect a bounding region including a face of a human, or a portion of a face of a human, within the image. From the bounding region, optical processing unit 350 may detect, using facial feature characteristics, facial symmetry knowledge, and other information, bounding regions depicting eyes of the human.

Some embodiments of the software may detect (e.g., in real time, like by monitoring frames of video from the phone's camera and classifying frames within less than 1 second, like within 500 ms, or 50 ms of the frame being received) the presence of recognizable human face, anterior eye, and posterior pole of the fundus detected through implementation of machine learning techniques and/or shallow deep learning architectures using the OpenCV and PyTorch libraries. Some embodiments may apply depth-separable convolutional neural networks to reduce computing resources needed to do on-device inference, e.g., with smartphones having fewer computing resources than a server, like with the MobileNetV3 algorithm described in a paper titled Searching for MobileNetV3 by Howard et al, in arXiv:1905.02244, the contents of which are hereby incorporated by reference in their entireties. Some embodiments may implement visual transformers, or other transformer networks, to detect and recognize certain anatomical features. As an example, features indicating the presence of an optic nerve in an image may be used to verify that the captured image is a valid image of the fundus, and can be passed to image quality assessment component 484, AI based classifier 486, or other components of processing unit 460 or image processing subsystem 114 for further analysis of the images.

In some embodiments, image quality assessment component 484 may be configured to compute a blurriness of an image to determine whether a captured image is capable of being used for further analysis. Some cases include image quality assessment component 484 computing a variance of the Laplacian of the image to quantify the blurriness of the image in order to adjust zoom and for use as an inclusion criteria. In some embodiments, image quality assessment component 484 may compute a blurriness score, or focus measure, using machine learning techniques accessible via the OpenCV or PyTorch libraries. To compute the blurriness score, an image may be convolved with the Laplacian kernel. To improve the speed of the computations, the image may be gray scaled prior to the convolutions, however separate RGB channels may also be used. From the convolved image, a variance may be computed to determine the blurriness score. In some embodiments, if the blurriness score may be compared to a blurriness threshold condition to determine whether the image is classified as being "blurry" or "not blurry." For example, if the blurriness score of a given image is less than a threshold blurriness score, then the image may be classified as "blurry," and may not be used for ocular disease analysis. If the blurriness score is greater than or equal to the threshold blurriness score, then the image may be classified as "not blurry," and that image may be used for ocular disease analysis. The variance of the Laplacian may be used to detect blurriness because images that are "in focus" will tend to have many well-defined edges, and therefore their variance is expected to be higher than images that are not "in focus," which tend to have less well-defined edges. The threshold blurriness score may be set in advance or may be dynamically configurable. As an example, the threshold blurriness score may be set to 100.

Returning to FIG. 1, image processing subsystem 114 may be configured to process captured images from wearable device 120. The captured images may be infrared images, visible images, or both, captured by imaging component 310. In some embodiments, image processing subsystem 114 may implement processing unit 460 to perform further image processing using an AI-based classifier 486.

After an image is captured and verified as a usable fundus photograph, it may be passed to an optimized, AI-based classifier system, which is also referred to herein as a trained computer vision model. The trained computer vision model may be implemented with deep convolutional neural networks, visual transformers, or other machine learning techniques.

In some embodiments, image processing subsystem 114 may perform data normalization steps to captured images (e.g., captured infrared images, captured visible images, or both). Some embodiments may also include image quality assessment component 484, or other components of wearable device 120 (e.g., optical processing unit 350), or components of client device 140, performing some or all of the image processing steps such as data normalization. In some embodiments, data normalization may include transforming each captured image into a grayscale image. Each captured grayscale image may be loaded into a 2D matrix resized to 342×342 px, then center-cropped to 299×299 px to remove borders. The matrix may then be normalized to the standard gaussian distribution to facilitate more effective convergence during training as well as better model generalizability to novel images.

As mentioned above with respect to model training subsystem 112, training a model for classifying images, such as infrared images depicting a retina of a patient, may include training a convolutional neural networks (CNN) to analyze and classify the images as depicting a retina having one or more retinal abnormalities or not having any retinal abnormalities. Some cases may include training a visual transformer, such as ViT, to analyze and classify the captured images. Using the PyTorch framework, some embodiments retrained several distinct CNN architectures pre-trained a large dataset, on a large dataset of fundus images, as detailed above with respect to FIGS. 2A and 2B (e.g., a second training stage performed by second model training logic 204). These models may be trained once more on a large dataset of infrared (IR) portable camera images, e.g., leveraging transfer learning techniques to learn a corrective downstream model that corrects errors in the transferred model or to adjust parameters of the transferred model. This training may refer to a third training step described above with respect to FIGS. 2A and 2B. Retraining may include initializing the convolutional layers with loaded pretrained weights along with a newly-initialized final, softmax layer and training this model to recognize selected classes. In order to fully optimize the model to the task, the lower convolutional layers may be initially frozen with the weights from the dataset and used as fixed feature extractors until training converged the top fully-connected layers, then the convolutional layers may be unfrozen, and the CNNs may be fine-tuned for several more epochs. Training of layers by backpropagation of errors may be performed by stochastic gradient descent. This may be repeated for the infrared (IR) dataset as well with each distinct CNN architecture.

Some embodiments may execute a gradient descent optimization to reduce the error rate and select appropriate neural network weights and biases during training. Some embodiments may train the model by, for example, initially assigning randomly weights, calculating an error amount with which the model describes the training data and a rates of change in that error as a function of the weights in the model in the vicinity of the current weight (e.g., a partial derivative for each model parameter of rate of change in error locally with respect to that dimension, or local slope); and incrementing the weights or biases in a downward (or error reducing) direction for each parameter. In some cases, these steps may be iteratively repeated until a change in error between iterations is less than a threshold amount, indicating at least a local minimum, if not a global minimum. To mitigate the risk of local minima, some embodiments may repeat the gradient descent optimization with multiple initial random values to confirm that iterations converge on a likely global minimum error. The resulting, trained model may be stored in memory and later retrieved for application to new calculations on out-of-sample data.

After obtaining the trained computer vision model, image ensembling may be performed. The image ensembling may include, for each eye evaluation, several captured images being individually evaluated by trained computer vision model. The final clinical recommendation, diagnoses, or result, made may be determined by averaging the softmax probabilities of the classifications of each image to ensure, or increase the likelihood of, maximum accuracy.

Trained convolutional neural networks of various architectures (e.g., InceptionV3, ResNet, DenseNet, MobileNetV3), trained visual transformers (e.g., ViT), or other computer vision models, may be redundantly ensembled for each image classification task. The final clinical recommendation made may be determined by averaging the softmax probabilities of the classifications of each distinct architecture to ensure, or increase the likelihood of, maximum accuracy, for instance, in an ensemble model.

In some embodiments, automated generation of a screening report including the captured image of the fundus, a point-of-interest heatmap, the screening classification determined by the AI classifier, and any other pertinent information may be performed. The purpose of this assessment is for use as a patient report to forward to a partnered reading center for human validation and follow-up appointment with a board-certified physician or specialist.

Figure 5A:
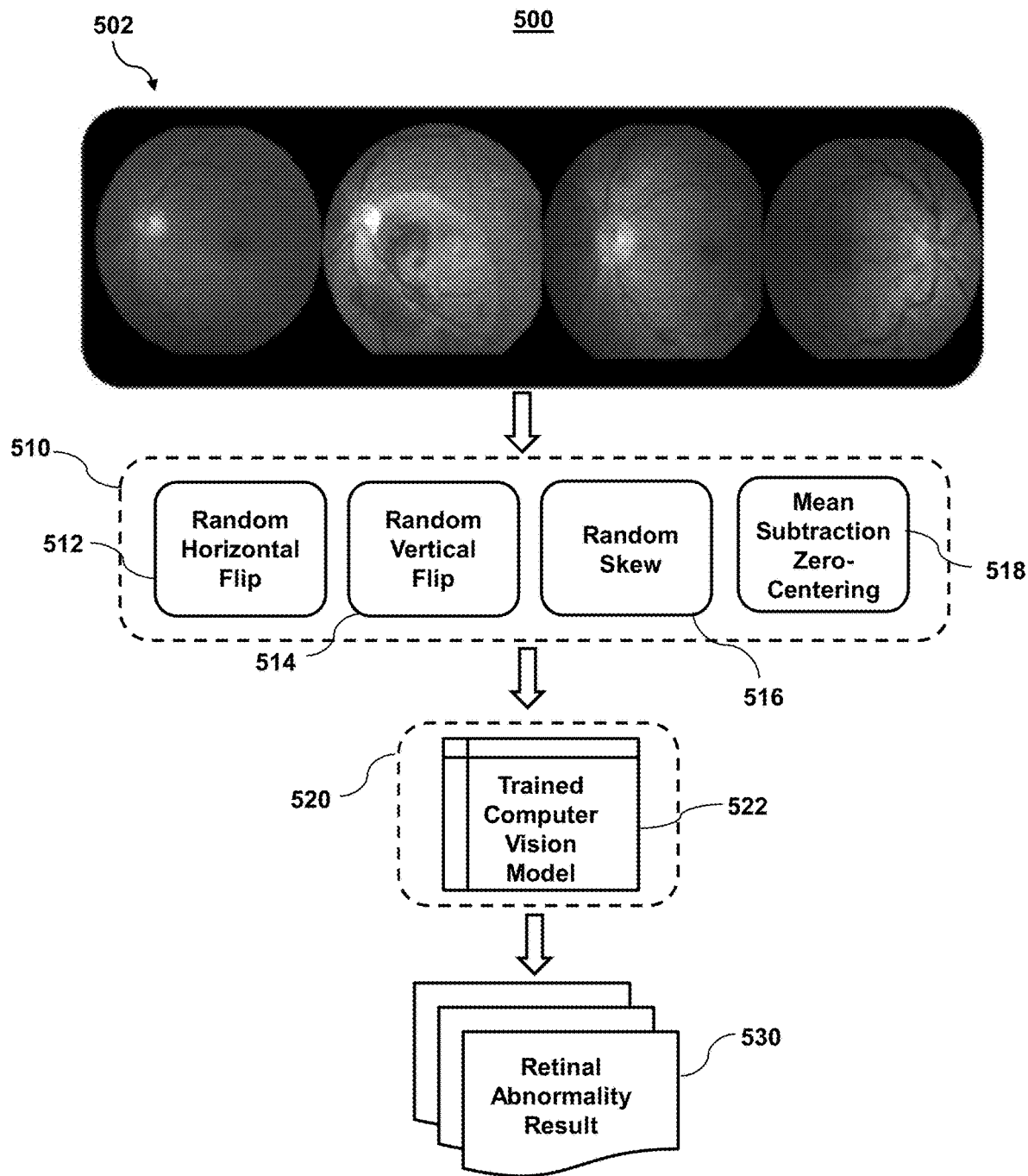
FIGS. 5A and 5B illustrate an example image processing subsystem, in accordance with various embodiments.
Figure 5B:
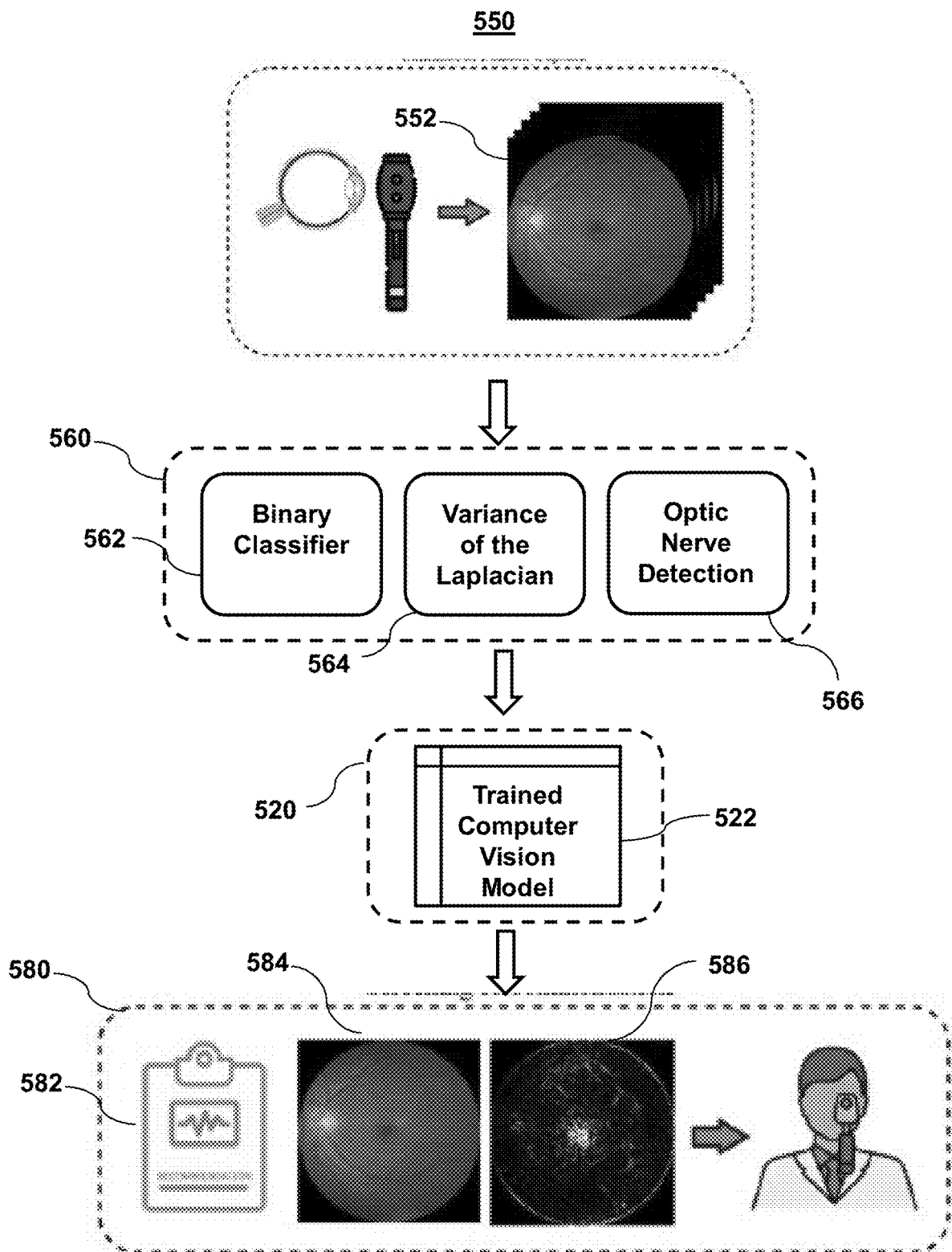

FIGS. 5A and 5B illustrate an example image processing subsystem, in accordance with various embodiments. FIG. 5A depicts an overview of a process 500 describing an example operation of the software algorithm. Initially, process 500 may include obtaining infrared images 502 captured by imaging component 310 of wearable device 120. As detailed above, wearable device 120 may include an infrared light source (e.g., infrared light source 454) and an infrared camera (e.g., imaging component 310), which are configured to capture images depicting a retina of a patient. For convenience, images 502 are illustrated as grayscale images, as infrared images may not be capable of being viewed by a human. Each of images 502 may depict a fundus of the patient's eye. In some embodiments, images 502, or data representing images 502 (e.g., each image may be stored as an array of pixel values, where each pixel value indicates an intensity of light detected by a corresponding pixel's sensor from imaging component 310). Images 502 may be stored in local memory of wearable device 120 and provided to computing system 102 upon request thereby for analysis and classification, or images 502 may be provided in real-time to computing system 102 from wearable device 120.

During a pre-processing stage 510, image processing subsystem 114 may be configured to perform one or more image processes to images 502. For example, pre-processing stage 510 may include one or more of the following processes being performed to images 502: random horizontal flip 512, a random vertical flip 514, a random skew 516, or mean subtraction zero-centering 518. Random horizontal flip 512 refers to a process whereby an image is horizontally flipped randomly with a given probability, which may be defined. Similarly, random vertical flip 514 refers to a process whereby an image is vertically flipped randomly with a given probability. Random skew 516 refers to a process whereby an image is randomly skewed based on a given probability. Mean subtraction, or zero-centering, refers to a process whereby a mean is subtracted from each data point in the image to make it zero-centered to optimize performance of a trained computer vision model. In some embodiments, the processes of random horizontal flip 512, random vertical flip 514, random skew 516, and mean subtraction zero-centering 518 may be implemented using the OpenCV or PyTorch libraries.

The pre-processed images may then be passed to an image processing stage 520. For instance, image processing subsystem 114 may be configured to implement various processes associated with image processing stage 520. In some embodiments, image processing stage 520 may include providing, as input, each pre-processed image from images 502 to a trained computer vision model 522. As mentioned above, trained computer vision model 522 may be trained using a multi-stage training process to be able to analyze infrared images and determine whether those images include any retinal abnormalities consistent with certain ocular diseases. Image processing subsystem 114 may be configured to execute, or facilitate the execution of, trained computer vision model 522 in response to the pre-processed version of images 502 being provided, as input, thereto. Trained computer vision model 522 may analyze the images and output one or more retinal abnormality results 530. In some embodiments, the output of trained computer vision model 522 may be indicate whether any retinal abnormalities are present within a given image. For instance, the output (e.g., retinal abnormality results) may indicate which images depict a retina including one or more retinal abnormalities consistent with certain ocular diseases. In some embodiments, retinal abnormality results 530 may indicate which, if any, ocular diseases a patient may have. For example, retinal abnormality results 530 may indicate whether the patient has diabetic retinopathy, as well as a confidence score associated with the classification.

FIG. 5B depicts another process 550 for using a trained computer vision model to determine whether a patient has one or more ocular diseases. Similar to process 500 of FIG. 5A, process 550 may begin with images 552 being obtained. In some embodiments, images 552 may be obtained via wearable device 120 (e.g., using imaging component 310), or images 552 may be captured by another imaging device capable of capturing infrared images of a patient's retina.

At a pre-processing stage 560, one or more pre-processing steps may be performed to images 552. In some embodiments, pre-processing stage 560 may include one or more modules configured to perform certain image transformations, analyses, or adjustments to some or all of images 552. Some embodiments include some or all of the pre-processing steps being performed be wearable device 120, client device 140, or image processing subsystem 114 of computing system 102. That is, depending on the hardware components and design, certain pre-processing steps may be offloaded from the server such that less data is transmitted from wearable device 120 or client device 140 across networks 150 to computing system 102.

Pre-processing stage 560 may include one or more binary classifiers 562. Each binary classifier may be configured to perform a quick and accurate check for certain image properties. The binary classifiers may be trained such that they have a minimal chance of false positives. In some embodiments, binary classifiers 562 may include a retina detection classifier configured to classify a given image as depicting a patient's retina or not depicting a patient's retina.

This may be used as an initial quality check to determine whether down-stream processes can be performed to the captured images. In some cases, the retina detection classifier may be trained to detect certain anatomical ocular features that are expected to be present in retinal images that are capable of being classified by the trained computer vision model. If the optical feature is not present in the captured images, then this indicates that the patient's eye (e.g., eye 302) will not be able to be used to detect retinal abnormalities. Certain contraindicators may also be detectable using binary classifiers 562. For example, binary classifiers 562 may be configured to determine whether a patient has cataracts based on images 552. Some example contraindicators that may be detectable by binary classifiers 562 include cataracts, infection, laser spots, previous diagnosis of DR, other objects that obscure the eye, and the like.

In some embodiments, pre-processing stage 560 may also include a blur score check 564. Blur score check 564 refers to one or more steps that may be performed to each of images 552 to ensure that images 552 are clear enough to be analyzed by the trained computer vision model. Blur score check 564 may include steps for computing a blur score, also referred to as a focus measure, for each of images 552, and determining, based on a respective blur score, whether a blur threshold condition is satisfied. Some cases include pre-processing stage 560 transforming each image (e.g., infrared image) from images 552 into a grayscale image. Converting an image to a grayscale image may include performing a weighted combination of a, e.g., pixel, value for each of the R, G, and B channels of the raw image. For example, a given pixel value from a pixel array representing the image may be based on three color input channels: red, green, and blue. The grayscale pixel value may be computed by averaging the pixel values of each color channel, using the luminosity technique, or using other grayscale conversion techniques. After obtaining a grayscale image for each of images 552, a Laplacian kernel applied to each grayscale image. The Laplacian kernel is a 3×3 matrix, e.g., {{0, 1, 0}, {1, −4, 1}, {0, 1, 0}}, that is convolved with the pixel value array of each image. After the Laplacian kernel is applied, a variance may be computed for each pixel. Images that have high variance typically represent images that are not blurry, whereas images that have low variances typically represent images that are blurry. This is because the Laplacian kernel and variance, similar to the Sobel kernel, can be used to detect how many edges are present in the image. The more edges there are, the higher the variance, as blurry images tend to not have many well defined edges. The blur score may be generated based on the variance. For instance, the blur score may be the variance. To determine whether the blur threshold condition is satisfied, a blur threshold score may be determined, either previously or dynamically, and the blur score for an image may be compared to the blur threshold score. If the blur score is greater than or equal to the blur threshold score, then the image may be classified as being not blurry. Images classified as being blurry (e.g., having a blur score less than the blur threshold score) may be removed from images 552 in some cases.

In some embodiments, pre-processing stage 560 may also include an optic nerve detection step 566, where a determination is made as to whether or not each of images 552 include an optic nerve. The optic nerve may be a characteristic optical feature used for determining whether a patient's retina displays any retinal abnormalities. In some embodiments, the optic nerve may be determined using a machine learning model trained to detect the optic nerve within images depicting patients' eyes. Similar to eye classifiers and other anatomical object recognition models, the optic nerve detection step 566 may include passing each of images 552 to an optic nerve detection model, and obtaining an output from the model indicating whether the optic nerve is present in the image. If the optic nerve is not present, then that image or images may be removed from images 552.

After pre-processing stage 560 performs the aforementioned quality checks, the filtered images (e.g., a subset of images obtained responsive to removal of one or more of images 552 during pre-processing stage 560) may be passed to image processing stage 520. In some embodiments, image processing stage 520 may include providing, as input, each processed image (e.g., the subset of images 552) to trained computer vision model 522. Trained computer vision model 522 may analyze the images and output one or more retinal abnormality results 530. In some embodiments, instead of, or in addition to, outputting retinal abnormality scores 530, trained computer vision model 522 may output a classification score 582 during a results analysis stage 580. Classification score 582 may indicate a likelihood that a patient has a particular ocular disease based on an analysis of each of the processed images. For example, classification score 582 may indicate that, based on the processed images analyzed using trained computer vision model 522, the patient likely has diabetic retinopathy. In some embodiments, one or more of the processed images, such as images 584, 586 may also be output by trained computer vision model 522 in addition to classification score 582. In some cases, images 584, 586 may depict one or more images provided the strongest contribution to trained computer vision model 522 outputting classification score 582. Classification score 582, images 584, 586, or other information, may be subsequently passed to a medical professional, medical service, or the patient, for additional review.

Figure 6:
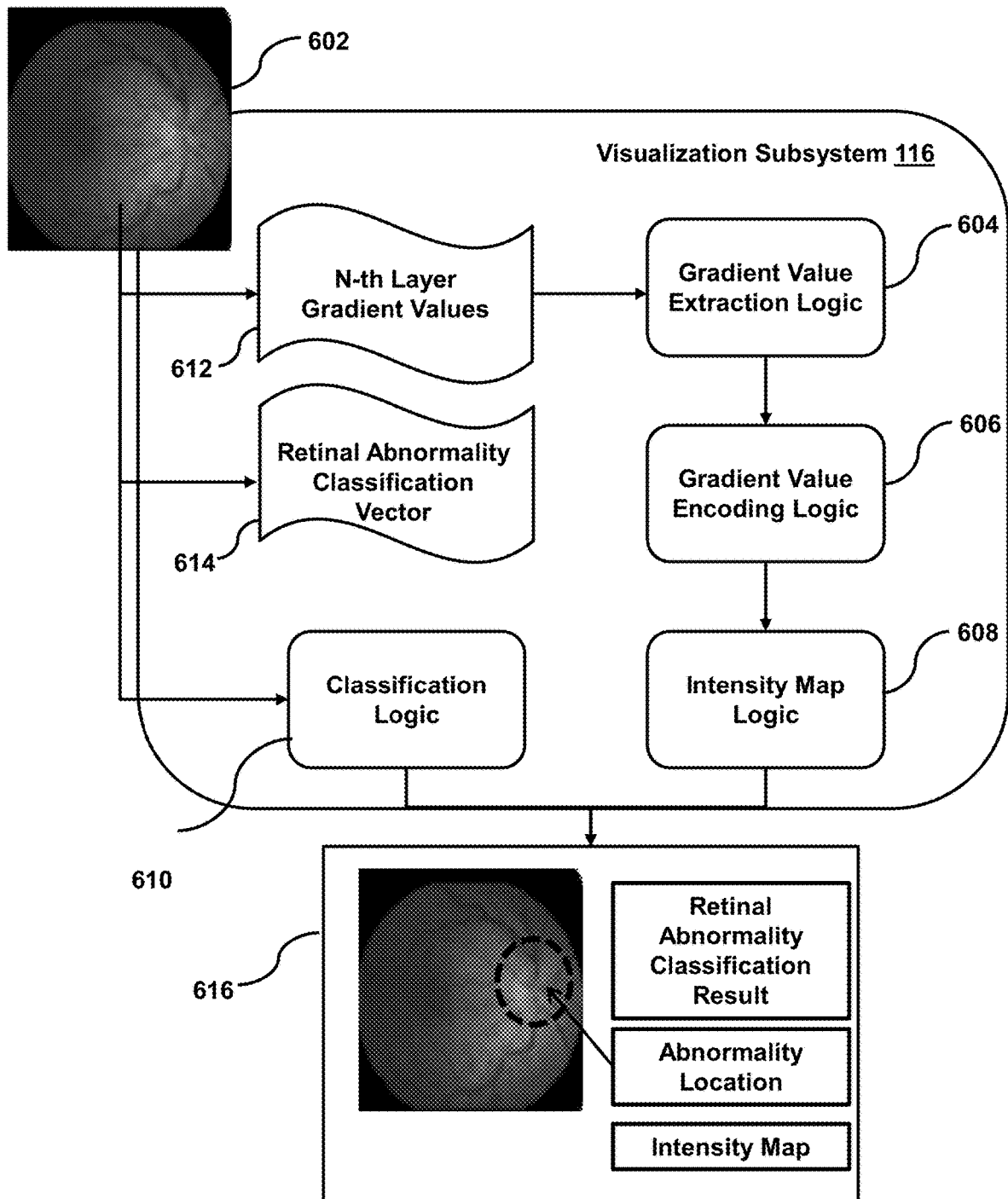
FIG. 6 illustrates an example visualization subsystem, in accordance with various embodiments.

Returning to FIG. 1, visualization subsystem 116 may be configured to analyze each image processed by the trained computer vision model, interpret a classification result output by the trained machine learning model, and extract information from the trained computer vision model to generate and output information for display to a patient, a medical provider, or other individuals. As an example, with reference to FIG. 6, visualization subsystem 116 may include gradient extraction logic, gradient value encoding logic, intensity map logic, and classification logic. In some embodiments, gradient extraction logic 604 may obtain n-th layer gradient values 612 for infrared image 602. In some embodiments, trained computer vision model 522 may be configured to compute a gradient at each layer. Trained computer vision model 522 may include N layers, where the N-th layer may include a classification of infrared image 602 to one of M different categories. For example, trained computer vision model 522 may, at a last layer, output a classification vector having M dimensions, where M represents a number of different possible classifications that trained computer vision model 522 can resolve infrared image 602. If a certain classification has a higher classification score in the classification vector, then this indicates that trained computer vision model 522 determined that infrared image 602 more likely represents that classification (e.g., diabetic retinopathy, healthy fundus) than the other possible classifications. N-th layer gradient values 612 may be extracted from the n-th layer via gradient extraction logic 604 to identify one or more portions of infrared image 602 that contributed most to the resolved classification. The gradients each relate to a particular pixel or set of pixels in infrared image 602, and there for the gradients have a highest value (or lowest value) indicate the greatest change from the N−1 layer to the N-th layer of trained computer vision model 522. Gradient extraction logic 604 may therefore extract the N-th layer gradient values, as well as, in some embodiments, additional layers' gradient values, to determine which pixel or pixels provided the greatest contribution to the resulting classification. Based on the pixel or pixels that most significantly contribute to the classification result, gradient value extraction logic may be configured identify the regions in infrared image 602 that most significantly contributed to trained computer vision model 522 classifying infrared image 602 into a given category.

In some embodiments, gradient value encoding logic 606 may encode extracted N-th layer gradient values 612 in response to being obtained by gradient extraction logic 604. Encoding n-th layer gradient values 612 may include transforming each gradient value into a hue value, grayscale value, or other representation based in a predefined mapping. For example, each gradient value may be assigned a hue (e.g., in an RGB color spectrum) such that different gradient values can be represented by different colors. As an example, lower gradient values may be assigned lower wavelength colors (e.g., blue), whereas higher gradient values may be assigned higher wavelength colors (e.g., red). As another example, lower gradient values may be assigned a grayscale value such that lower gradient values may have a lower grayscale value (e.g., little to no grayscale or white), while higher gradient values may have a higher grayscale value (e.g., dark). In some embodiments, gradient value encoding logic 606 may be configured to identify, from n-th layer gradient values 612, which regions within infrared image 602 have a greatest gradient value. Gradient value encoding logic 606 may generate bounding boxes (or other shapes) to encompass these regions, and metadata indicating a pixel location within infrared image 602 of the bounding boxes may be generated and stored in association with infrared image 602. In this way, an enhanced infrared image 616, which refers to an enhanced version of infrared image 602, may be generated based on the metadata, encoding, or other data, as described below.

Intensity map logic 608 may be configured to generate an intensity map for infrared image 602 based on the encoded gradient values. The intensity map, which is also referred to herein interchangeably as a "heat map," depicts infrared image 602 with different colors/hues/grayscale values to represent which portions of infrared image 602 have a greatest gradient value at the N-th layer of trained computer vision model 522. Intensity map logic 608 may generate the intensity map by determining the pixel location of each encoded gradient value. For example, if infrared image 602 is 255×255 px, then, for each pixel, or a subset of pixels, intensity map logic 608 may determine the encoded gradient value for that corresponding pixel, and generate the intensity map based on the encoded gradient value. Intensity map logic 608 may output an intensity map as part of enhanced infrared image 616. The intensity map may be overlayed onto infrared image 602, or, alternatively, the intensity map may be its own image that is output in addition to infrared image 602. In some embodiments, the intensity map may also include the abnormality location to indicate where a particular abnormality is located within the intensity map. Enhanced infrared image 616 may therefore allow an individual, e.g., the patient, medical practitioner, to not only view infrared image 602, but also view the intensity map and abnormality location information.

Classification logic 610 may be configured to output a classification vector 614, classification result, or both, indicating whether infrared image 602 includes any retinal abnormalities. In some cases, classification logic 610 may obtain a classification vector 614 or classification result, and may translate classification vector 614 or result into a diagnoses of an ocular disease or lack of an ocular disease. For instance, classification logic 610 may obtain a classification vector indicating that infrared image 602 depicts a retina having a first type of retinal abnormality. Based on trained knowledge that retinas having the first type of retinal abnormality typically are associated with a first ocular disease, classification logic 610 may output a retinal abnormality classification result including the first ocular disease, as well as, or alternatively, the first type of retinal abnormality, with enhanced infrared image 616.

Figure 7A:
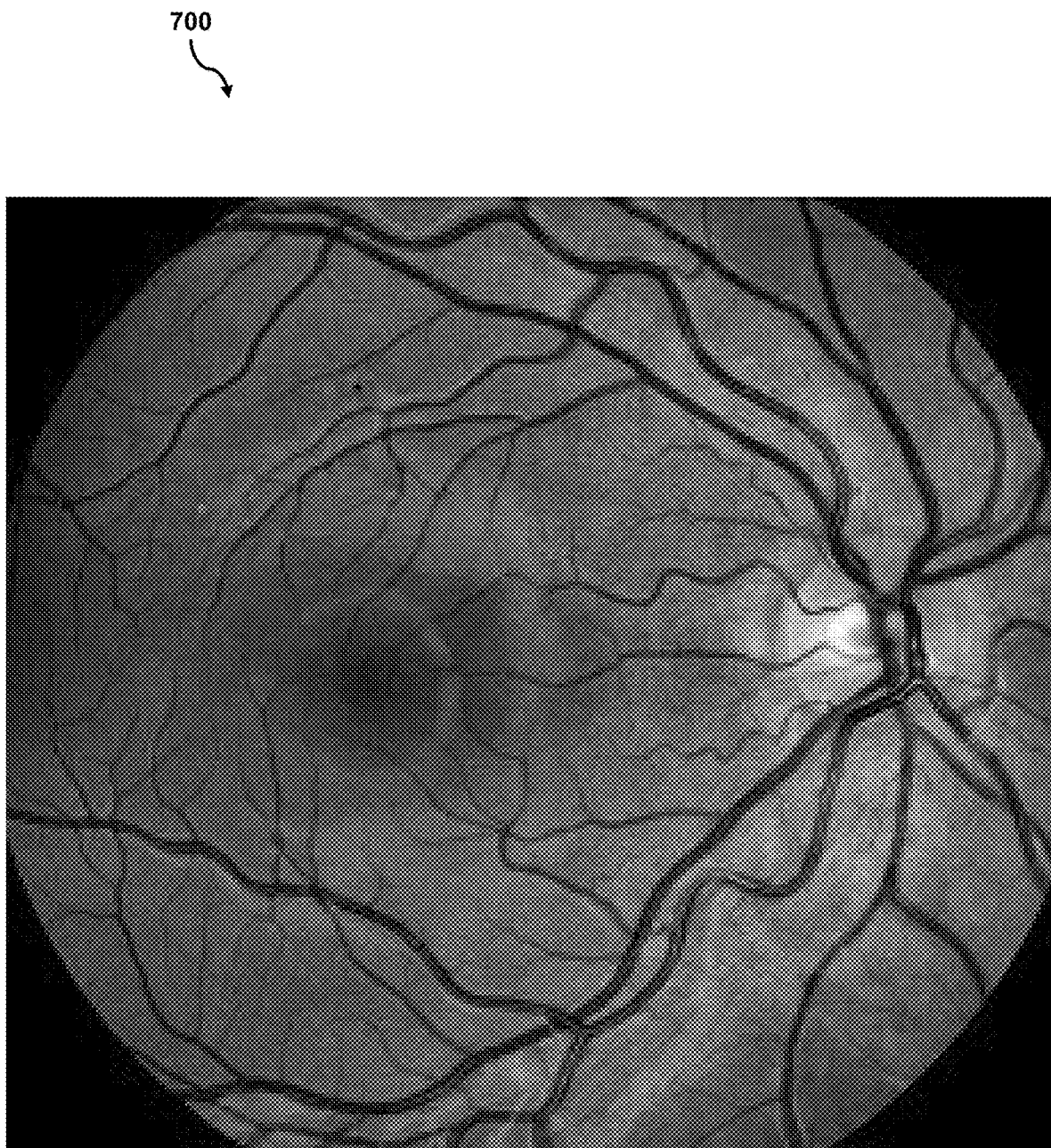
FIGS. 7A-7B are illustrative diagrams of example healthy and unhealthy retina, in accordance with various embodiments.
Figure 7B:
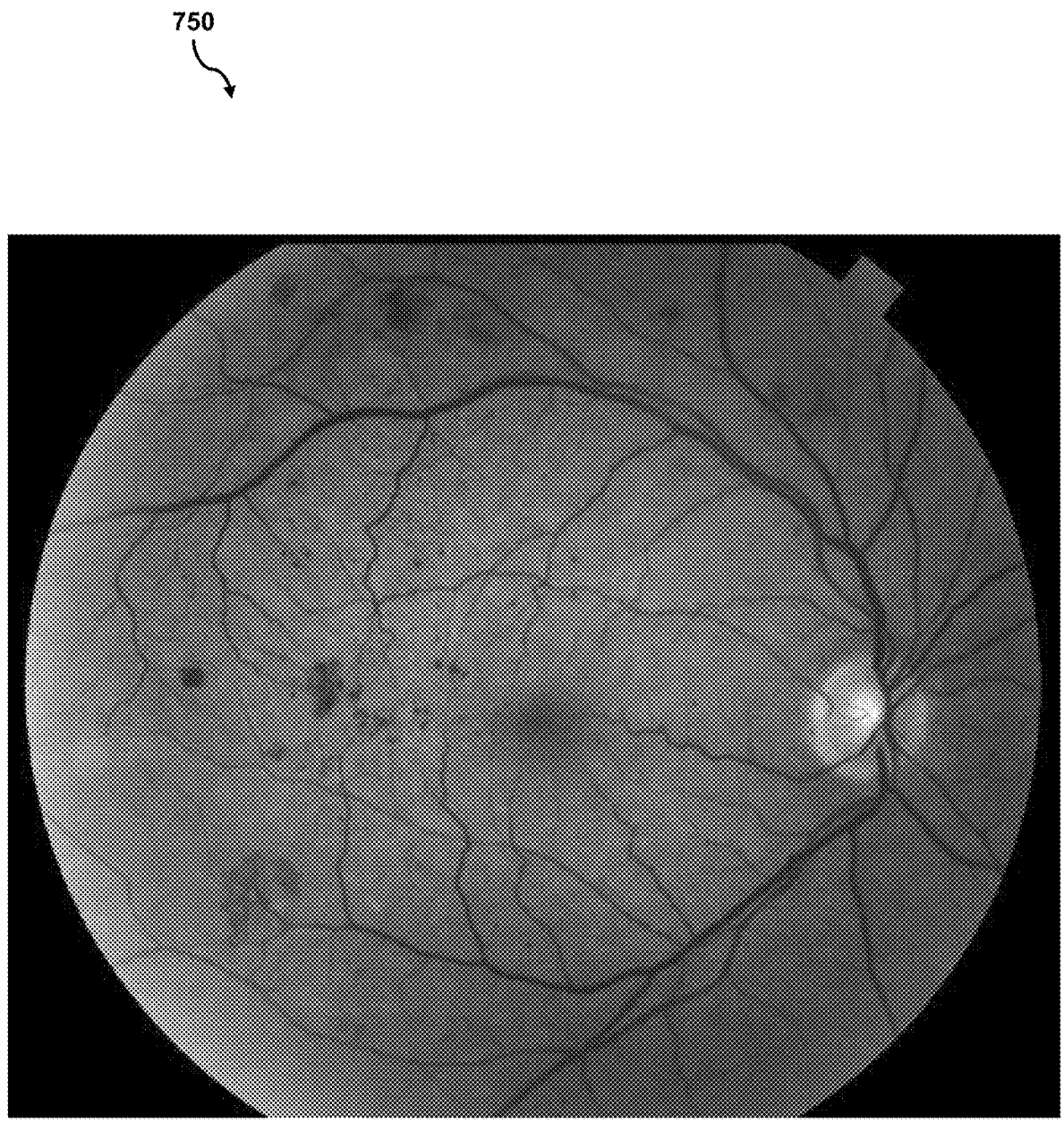

FIGS. 7A-7B are illustrative diagrams of example healthy and unhealthy retina, in accordance with various embodiments. Retinas with diabetic retinopathy may display vascular etiologies such as small dot hemorrhages, microaneurysms, and exudates, while healthy retinas will be free from these etiologies and display the hallmarks of a healthy retina, centered macula, and an optic nerve with appropriate cup to disc ratio, among other hallmarks.

Example Flowcharts

Figure 8:
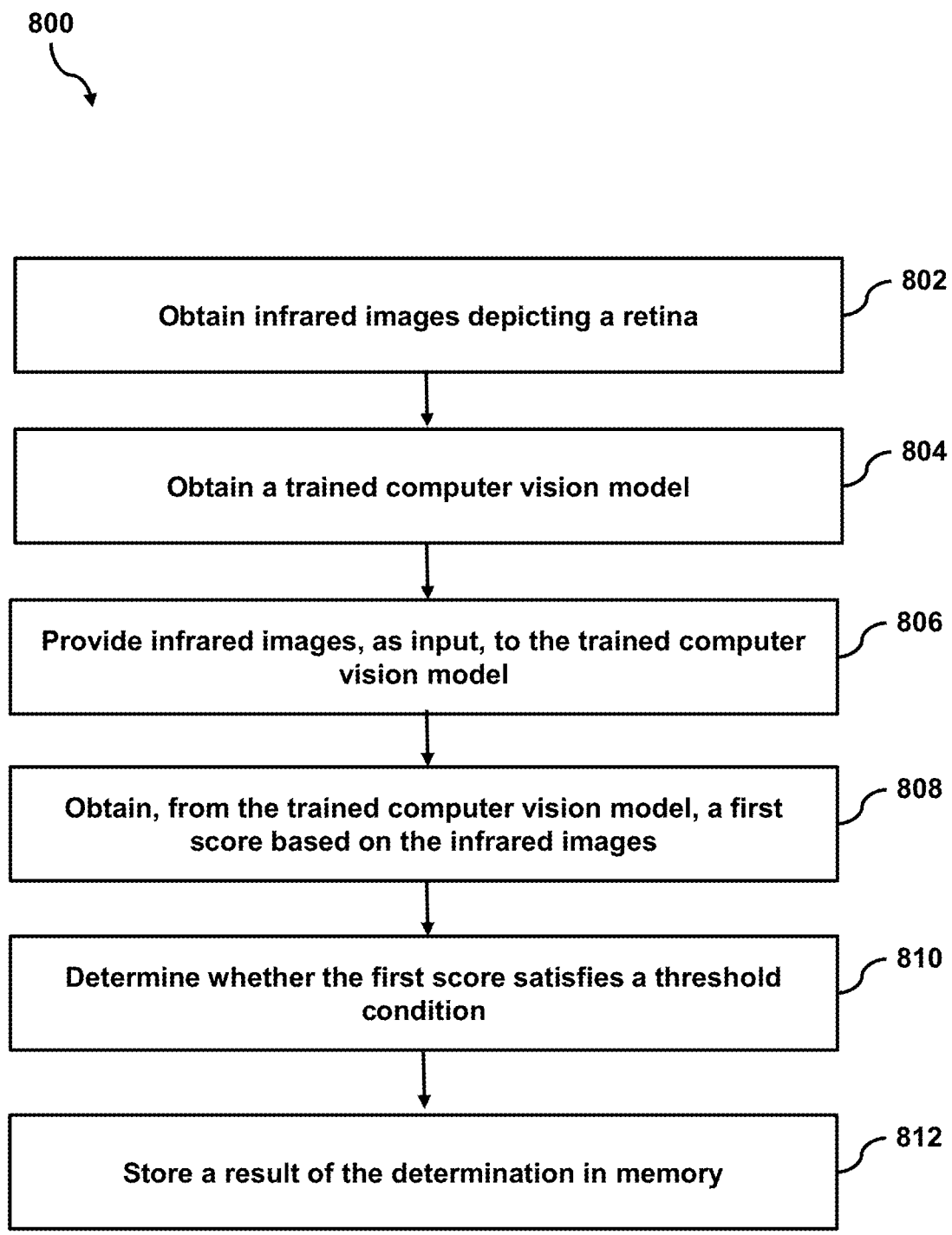
FIG. 8 illustrates an example process for analyzing infrared images depicting a patient's retina to detect retinal abnormalities, in accordance with various embodiments.
Figure 9:
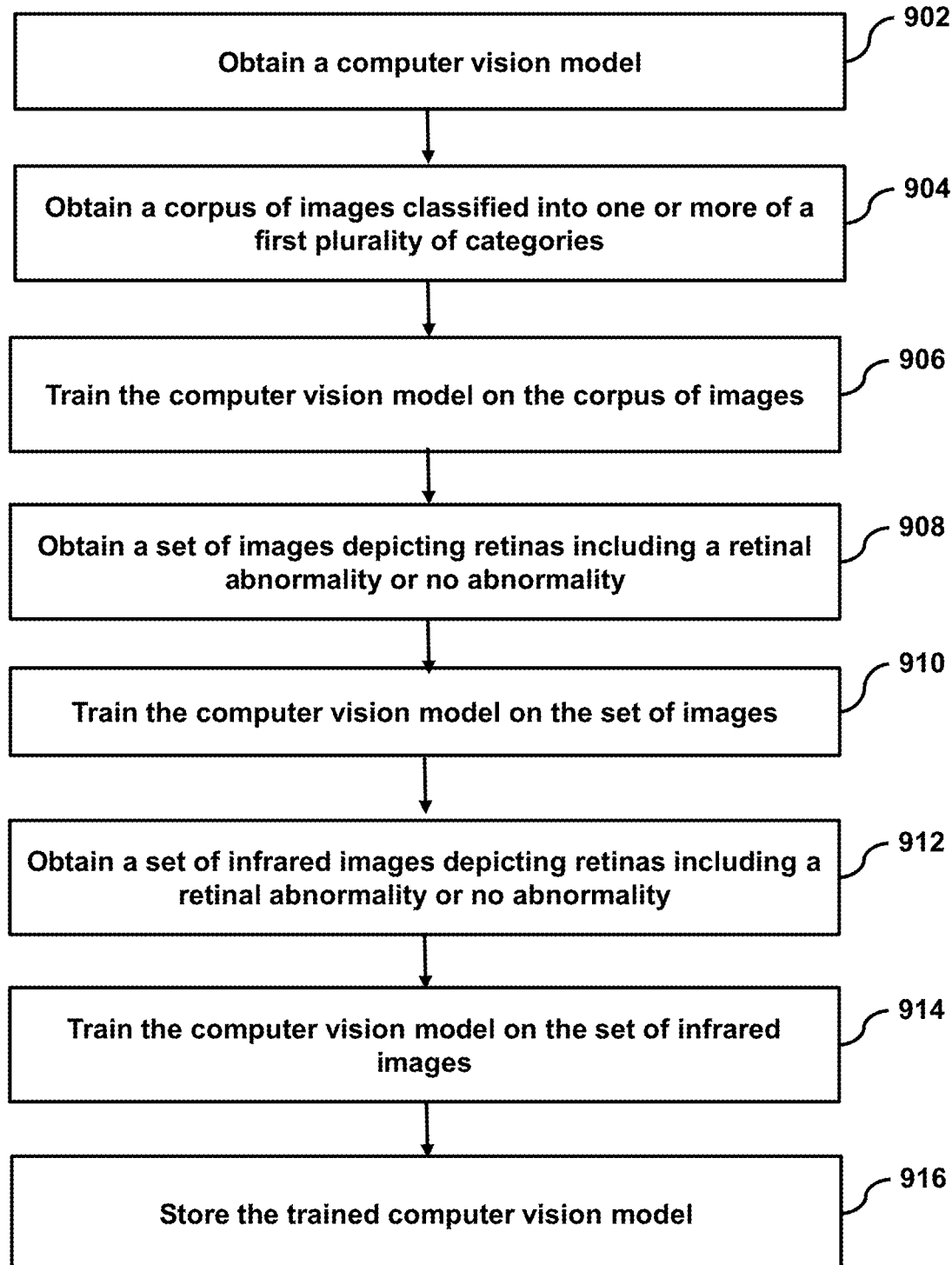
FIG. 9 illustrates an example process for training a computer vision model to identify retinal abnormalities in infrared images of a patient's retina, in accordance with various embodiments.

FIGS. 8-9 are example flowcharts of processing operations of methods that enable the various features and functionality of the system as described in detail above. The processing operations of each method presented below are intended to be illustrative and non-limiting. In some embodiments, for example, the methods may be accomplished with one or more additional operations not described, and/or without one or more of the operations discussed. Additionally, the order in which the processing operations of the methods are illustrated (and described below) is not intended to be limiting.

In some embodiments, the methods may be implemented in one or more processing devices (e.g., a digital processor, an analog processor, a digital circuit designed to process information, an analog circuit designed to process information, a state machine, and/or other mechanisms for electronically processing information). The processing devices may include one or more devices executing some or all of the operations of the methods in response to instructions stored electronically on an electronic storage medium. The processing devices may include one or more devices configured through hardware, firmware, and/or software to be specifically designed for execution of one or more of the operations of the methods.

FIG. 8 illustrates an example process 800 for analyzing infrared images depicting a patient's retina to detect retinal abnormalities, in accordance with various embodiments. Process 800 may begin at operation 802. In operation 802, infrared images depicting a retina may be obtained. In some embodiments, infrared images may be captured by an infrared imaging component. A wearable device, such as, e.g., a headset, may include an infrared imaging component, as well as an infrared light source. In some cases, the wearable device may, when worn by an individual, create a substantially light-leakproof seal such that ambient light in the visible portion of the electromagnetic spectrum is prevented from leaking into a volume formed by the wearable device's adornment to the individual. In some embodiments, the infrared imaging component may capture one or more infrared images of a patient's eye, and, in particular, the fundus of the eye, using infrared light output by the infrared light source. The infrared images may be captured responsive to a manually trigger, a preset timer (e.g., capture X images within the first 30 seconds of wearing the device), or responsive to a determination that the infrared imaging component is oriented (e.g., so that the infrared imaging component is directed at a center of the patient's eye to capture images of the retina). In some embodiments, the captured infrared images may be provided to a computing system, such as computing system 102, for processing. In some embodiments, computing system 102 may perform pre-processing to the captured images to remove images that will not be useable downstream in the analysis process. Alternative or additionally, some pre-processing steps may be performed by computing system 102. In some embodiments, operation 802 may be performed by a subsystem that is the same or similar to image processing subsystem 114.

In an operation 804, a trained computer vision model may be obtained. In some embodiments, a multi-stage training process may be used to train the obtained computer vision model. For example, and as detailed above with respect to FIG. 2A, during a first training stage, a model may be trained using a large corpus of images relating to concepts different then the desired purpose of the trained computer vision model. For example, during a first training stage, a machine learning model, e.g., a CNN, visual transformer, may be trained using a large corpus of images pre-classified into one or more of a large number of categories, e.g., "Cats," "Dogs," "Cars," etc. The first training stage may be used to train the weights and biases of the lower layers of the model. During a second training stage, the initially or first trained (e.g., after being trained on the large corpus of images) computer vision model may be trained on a set of images depicting one or more of a plurality of retinal abnormalities, ocular diseases, both, or other topic-specific domains. During a third training stage, the first trained (e.g., after being trained on the large corpus of images and the set of images) computer vision model may be trained on a set of infrared images. The set of infrared images may include a plurality of infrared images depicting one or more of a plurality of retinal abnormalities, ocular diseases, or both. After the third training stage, the trained computer vision model may be stored in model database 136. In some embodiments, operation 804 may be performed by a subsystem that is the same or similar to model training subsystem 112, image processing subsystem 114, or a combination thereof.

In an operation 806, the captured infrared images may be provided, as input, to the trained computer vision model. The trained computer vision model may be trained to detect whether each captured infrared image depicts a retina including any retinal abnormalities, determine whether the patient has any ocular diseases, or both. The captured infrared images may be provided to the trained computer vision model, sequentially or in parallel. In some embodiments, operation 806 may be performed by a subsystem that is the same or similar to image processing subsystem 114.

In an operation 808, a first score may be obtained from the trained computer vision model based on the infrared images. In some embodiments, the first score may be computed by the trained computer vision model based on a classification score of each captured infrared image. For example, the trained computer vision model may output a classification vector for each infrared image, and where each element of the classification vector represents a classification score for a particular category of a plurality of possible categories (e.g., possible retinal abnormalities that can be detected within the captured infrared images, possible ocular diseases that can be identified from the captured infrared images, etc.). Based on the classification score for each respective infrared image, the first score may be computed. For example, the classification score for a first category of each captured infrared image may be averaged, to obtain an overall classification score for that category based on the captured infrared images. The overall classification score for each of the categories may then be compared to one another to determine a top N highest ranked indicating a most likely classification for the captured infrared images. The obtained first score may be a top-ranked overall classification score, an average of one or more scores, or another score from the computed classification scores. In some embodiments, operation 808 may be performed by a subsystem that is the same or similar to image processing subsystem 114.

In an operation 810, a determination may be as to whether the first score satisfies a threshold condition. In some embodiments, the threshold condition may be satisfied if a classification score is greater than or equal to a threshold classification score. If so, then the classification by the trained computer vision model may be assigned to the captured infrared images. For example, the trained computer vision model may generate a classification vector for the captured infrared images, and the classification vector may include a classification score for each of a plurality of categories. If one or more of the classification scores is greater than or equal to the threshold classification score, then those classification scores may satisfy the threshold condition. In some embodiments, a top classification score from the classification vector may be selected and compared to the threshold condition. If the top classification score satisfies the threshold condition, then the category associated with that classification score may be assigned as the retinal abnormality or ocular disease (or lack thereof) that the patient's retina depicts. In some embodiments, operation 810 may be performed by a subsystem that is the same or similar to image processing subsystem 114.

In operation 812, a result of the determination may be stored in memory. The result may include whether the captured infrared images depicts a particular retinal abnormality, ocular disease, or lack thereof. In some embodiments, the results may include an intensity map depicting locations within some or all of the captured images that contributed most the classification score assigned to the captured images. In some embodiments, operation 812 may be performed by a subsystem that is the same or similar to image processing subsystem 114.

FIG. 9 illustrates an example process 900 for training a computer vision model to identify retinal abnormalities in infrared images of a patient's retina, in accordance with various embodiments. In some embodiments, process 900 may begin at operation 902. In operation 902, a computer vision model may be obtained. The computer vision model may be untrained or it may be a previously trained model that needs to be re-trained. In some embodiments, the computer vision model to be trained is a convolutional neural network, a recurrent neural network, a visual transformer model, or other machine learning models, or combinations thereof. In some embodiments, operation 902 may be performed by a subsystem that is the same or similar to model training subsystem 112.

In operation 904, a corpus of images classified into one or more of a first plurality of categories may be obtained. The corpus of images may include more than 1 million images, more than 10 million images, more than 100 million images, or more. For example, the corpus of images may be include images selected from the dataset. The images may depict objects/scenes/contexts related to categories differing from those that the trained computer vision model is to be used for. For example, the images in the corpus may depict objects, and be pre-classified into categories related to categories, such as dogs, cats, cars, baseball, etc. Each image in the corpus of images may include one or more labels indicating a category or categories with which the respective image corresponds. In some embodiments, operation 904 may be performed by a subsystem that is the same or similar to model training subsystem 112.

In operation 906, the obtained computer vision model may be trained on the corpus of images. For example, the obtained computer vision model may undergo a first training based on the corpus of images obtained. The first training stage may allow the model to learn the weights and biases of the lower layers of the model. In some embodiments, operation 906 may be performed by a subsystem that is the same or similar to model training subsystem 112.

In operation 908, a set of images depicting retinas including a retinal abnormality, or not including a retinal abnormality, may be obtained. For example, set of images 212 may be obtained from training data database 134. Each image in the set of images may be pre-classified into one or more categories each associated with a given retinal abnormality or ocular disease. In some embodiments, operation 908 may be performed by a subsystem that is the same or similar to model training subsystem 112.

In operation 910, the first trained computer vision model may be trained a second time using the set of images. The second stage training may further refine the weights and biases of the lower layers of the model, while also refining the weights and biases of the upper layers of the models. The second trained computer vision model may be capable of detecting retinal abnormalities within (non-infrared) images. In some embodiments, operation 910 may be performed by a subsystem that is the same or similar to model training subsystem 112.

In operation 912, a set of infrared images depicting retinas including retinal abnormalities or no retinal abnormalities may be obtained. The set of infrared images include infrared images pre-classified as depicting one or more retinal abnormalities or ocular diseases, and may include labels associated with each classification. In some embodiments, the set of infrared images may include fewer images (e.g., less than 10,000 infrared images, less than 1,000 infrared images, or less) than the set of (non-infrared) images used for the second stage of training (e.g., less than 1,000,000 images, less than 100,000 images, less than 10,000 images, or less), and the set of images may include fewer images than the corpus of images. In some embodiments, operation 912 may be performed by a subsystem that is the same or similar to model training subsystem 112.

In operation 914, the second trained computer vision model may be trained a third time using the set of infrared images. The third stage training may further refine the weights and biases of the lower layers of the model, while also further refining the weights and biases of the upper layers of the models. The third trained computer vision model may be capable of detecting retinal abnormalities within infrared images. In some embodiments, operation 914 may be performed by a subsystem that is the same or similar to model training subsystem 112.

In operation 916, the trained computer vision model (e.g., the third trained computer vision model) may be stored in memory. For example, the trained computer vision model may be stored in model database 136. The trained computer vision model may be retrieved for use in determining whether any captured infrared images (e.g., obtained using an infrared imaging component of a wearable device) depict a retina having a retinal abnormality or ocular disease. In some embodiments, operation 916 may be performed by a subsystem that is the same or similar to model training subsystem 112.

Figure 10:
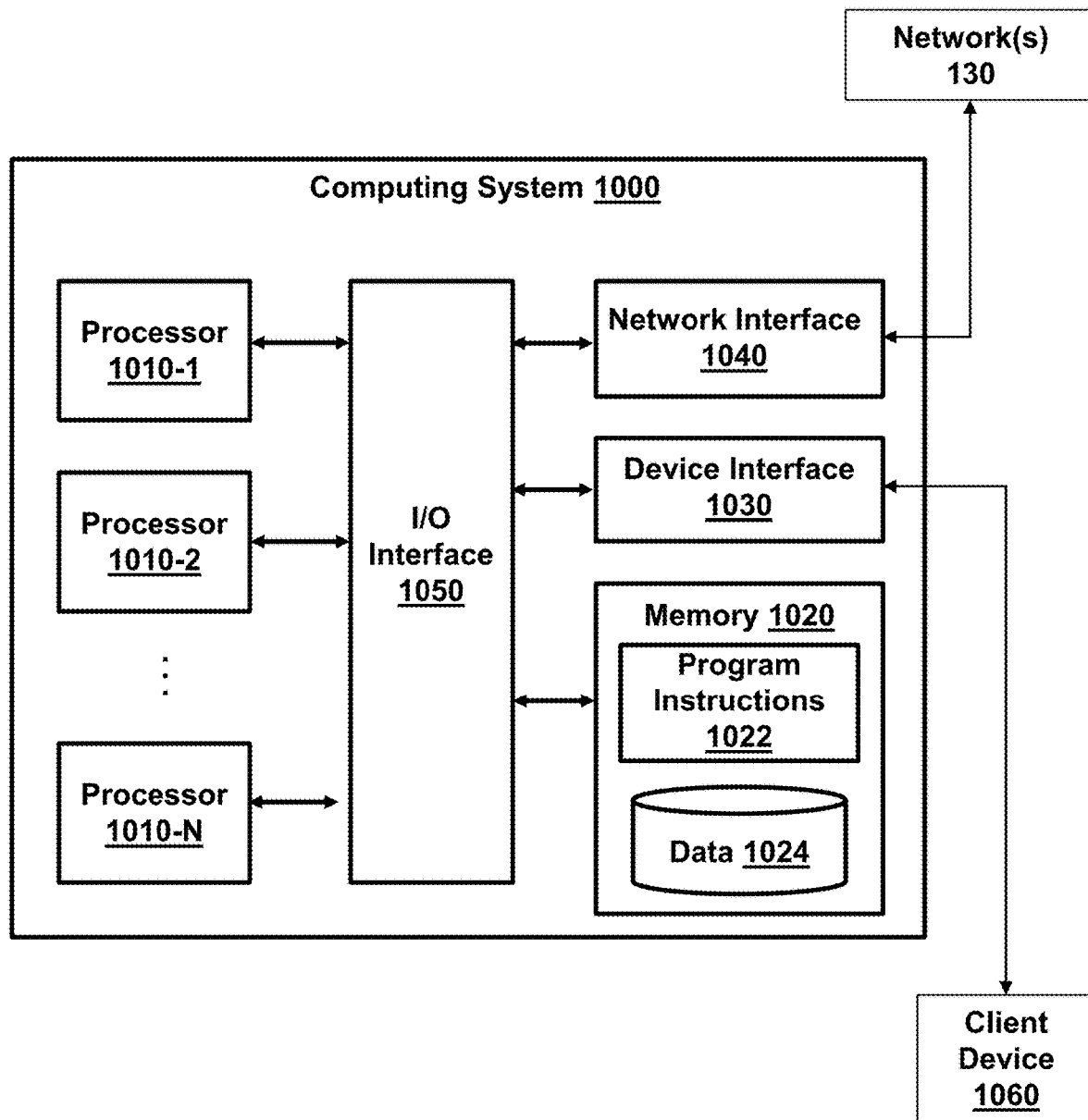
FIG. 10 is an example block diagram of a computing system upon which described program code may be executed, in accordance with various embodiments.

FIG. 10 is a diagram that illustrates an exemplary computing system 1000 in accordance with embodiments of the present technique. Various portions of systems and methods described herein, may include or be executed on one or more computer systems similar to computing system 1000. Further, processes and modules described herein may be executed by one or more processing systems similar to that of computing system 1000.

Computing system 1000 may include one or more processors (e.g., processors 1010-1 to 1010-N) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010-1), or a multi-processor system including any number of suitable processors (e.g., 1010-1 to 1010-N). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1000 may include a plurality of computing devices (e.g., distributed computer systems) to implement various processing functions.

I/O device interface 1030 may provide an interface for connection of one or more I/O devices 1060 to computing system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computing system 1000 through a wired or wireless connection. I/O devices 1060 may be connected to computing system 1000 from a remote location. I/O devices 1060 located on remote computer system, for example, may be connected to computing system 1000 via a network and network interface 1040. The Device Interface in some embodiments can be wire connected to the client device as depicted in FIG. 9. In some other embodiments the device interface may be connected to the client device wirelessly. In some wireless embodiments, the computing system is implemented in the cloud.

Network interface 1040 may include a network adapter that provides for connection of computing system 1000 to a network. Network interface may 1040 may facilitate data exchange between computing system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1022 or data 1024. Program instructions 1022 may be executable by a processor (e.g., one or more of processors 1010-1 to 1010-N) to implement one or more embodiments of the present techniques. Instructions 1022 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 may include a non-transitory computer readable storage medium that may have program instructions stored thereon that are executable by a computer processor (e.g., one or more of processors 1010a-1010n) to cause the subject matter and the functional operations described herein. A memory (e.g., system memory 1020) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 1050 may be configured to coordinate I/O traffic between processors 1010-1 to 1010-N, system memory 1020, network interface 1040, I/O devices 1060, and/or other peripheral devices. I/O interface 1050 may perform protocol, timing, or other data transformations to convert data signals from one component (e.g., system memory 1020) into a format suitable for use by another component (e.g., processors 1010-1 to 1010-N). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computing system 1000 or multiple computing systems 1000 configured to host different portions or instances of embodiments. Multiple computing systems 1000 may provide for parallel or sequential processing/execution of one or more portions of the techniques described herein.

Those skilled in the art will appreciate that computing system 1000 is merely illustrative and is not intended to limit the scope of the techniques described herein. Computing system 1000 may include any combination of devices or software that may perform or otherwise provide for the performance of the techniques described herein. For example, computing system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computing system 1000 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computing system 1000 may be transmitted to computing system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

The present techniques will be better understood with reference to the following enumerated embodiments:

1. An system, comprising: a wearable fundus camera configured to be worn as a headset by a human, the wearable fundus camera comprising: an infrared light source configured to output infrared light to be directed at a retina of the human; an image sensor configured to capture infrared images depicting a retina of an eye of the human under illumination from the infrared light source without a pupil of the eye being dilated with mydriatics; an eye cuff configured to be biased against a face of the human and occlude at least some ambient light from reaching the image sensor, wherein: the wearable fundus camera weighs less than 2 kilograms and has a center of mass less than 10 centimeters from a portion of the eye cuff configured to be positioned adjacent a bridge of the human's nose when worn by the human; a computing system storing computer program instructions that, when executed by the computing system, effectuate operations comprising: obtaining at least some of the captured infrared images depicting the retina of the human; obtaining access to a trained computer vision model configured to detect ophthalmologic abnormalities in retinal images; providing the at least some of the captured infrared images, as input, to the trained computer vision model; obtaining, from the trained computer vision model, based on the at least some of the captured infrared images, a first score indicating whether the at least some of the captured infrared images depict an ophthalmologic abnormality and storing, in memory, a result of the based on the score.

2. The system of embodiment 1, wherein the operations comprise: pretraining the computer vision model with a first training set of images to form a pre-trained computer vision model, at least 90% of the images in the first training set not being retinal images; training the pre-trained computer vision model with a second training set of labeled images, at least half of the labeled images in the second training set not being retinal images labeled according to whether the respective labeled images depict retinopathy; and determining the first score.

3. The system of embodiment 1, wherein: the trained computer vision model is trained on a corpus of images comprising images depicting a plurality of objects, each of the plurality of objects being classified into one or more first categories of a first plurality of categories, wherein each image from the corpus of images includes one or more first labels, each of the one or more first labels indicating that a respective image has been classified into one of the one or more first categories, the trained computer vision model is trained on a set of images comprising images depicting a plurality of retinas, each of the plurality of retinas being classified into one or more second categories of a second plurality of categories, wherein each image from the set of images includes one or more second labels, each of the one or more second labels indicating that a respective image has been classified into one of the one or more second categories, wherein each of the second plurality of categories include a subset of images from the set of images depicting a type of ophthalmologic abnormality or ophthalmologic normality, the type of ophthalmologic abnormality being one of a plurality of ophthalmologic abnormalities, and the trained computer vision model is trained on a set of infrared images comprising infrared images depicting retinas, wherein each infrared image from the set of infrared images is classified into at least one of the second plurality of categories, wherein each infrared image from the set of infrared images includes at least one of the one or more second labels.

4. The system of embodiment 3, wherein: the corpus of images includes more than 1 million images; the first plurality of categories includes more than 1 thousand categories; the set of images includes more than 1 hundred thousand images; the second plurality of categories includes ten or more categories; and the set of infrared images includes 1 hundred or more infrared images.

5. The system of embodiment 1, wherein the wearable fundus camera further comprises: one or more actuators configured to orient the infrared light source, wherein the infrared light source is oriented in response to determining that the infrared light is directed to a center of a pupil of an eye of the human when the wearable fundus camera is worn by the human, wherein the operations further comprise: identifying, based on at least one captured infrared image from the captured infrared images, using a first classifier configured detect an eye within an infrared image, a set of pixels representing a first portion of the at least one captured infrared image depicting the eye of the human; identifying, using a second classifier configured to detect the pupil within the at least one captured infrared image, a subset of pixels from the set of pixels representing a second portion of the at least one captured infrared image depicting the pupil of the eye of the human, wherein the first portion of the at least one captured infrared image comprises the second portion of the at least one captured infrared image; and determining, based on the subset of pixels, a location of the center of the pupil; and causing the one or more actuators to adjust a position of the infrared light source such that the infrared light output by the infrared light source is directed at the location of the center of the pupil.

6. The system of embodiment 1, wherein the operations further comprise: providing one or more additional captured infrared images to one or more binary classifiers, wherein the one or more additional captured infrared images are captured prior to the image sensor capturing the infrared images, wherein each of the one or more binary classifiers is configured to detect whether the retina depicted by the captured infrared images represents a respective contraindicator from a set of contraindicators; preventing the one or more additional captured infrared images from being analyzed by the trained computer vision model in response to detecting a given contraindicator; and causing the image sensor to capture the infrared images.

7. The system of any one of embodiments 1-6, wherein the wearable fundus camera comprises at least part of the computer system.

8. The system of any one of embodiments 1-6, wherein the infrared light includes incoherent light of multiple infrared wavelengths, the operations further comprise: selecting, for each of the multiple infrared wavelengths, a subset of the captured infrared images, wherein each subset of the captured infrared images includes infrared images of a respective infrared wavelength, wherein providing the captured infrared images to the trained computer vision model comprises: providing each subset of the captured infrared images to the trained computer vision model, wherein the first score is computed based on a weighted combination of a score output by the trained computer vision model for each subset of the captured infrared images.

9. The system of any one of embodiments 1-6, wherein the image sensor captures a plurality of infrared images, the captured infrared images being some of the plurality of infrared images, wherein the wearable fundus camera further comprises: memory storing additional computer program instructions; and one or more processors that, in response to executing the additional computer program instructions, effectuate additional operations comprising: providing the plurality of infrared images to a classifier trained to detect whether a given image depicts a retina of a human; and filtering the plurality of infrared images based on results of the classifier to obtain the infrared images.

10. The system of any one of embodiments 1-6, wherein the wearable fundus camera further comprises: one or more computer processors configured to: compute a blur score for each infrared image of the captured infrared images, wherein the blur score indicates how blurry a respective infrared image is, the blur score being computed by: transforming a given infrared image into a grayscale infrared image, applying a Laplacian kernel to an array of pixel values representing the grayscale infrared image, and computing a variance of each pixel value from the array of pixel values, and generating, for the given infrared image, the blur score based on the variance of each pixel value from the array of pixel values; determine whether a respective blur score is satisfies a threshold; removing one or more infrared images from the captured infrared images in response to determining that the respective blur score of the one or more infrared images satisfies the threshold.

11. The system of any one of embodiments 1-6, wherein the wearable fundus camera further comprises: means for outputting visible light directed at the retina of the human; and means for capturing a set of visible-light images depicting the retina of the human, wherein the score is further determined based on the set of visible-light images.

12. The system of any one of embodiments 1-6, wherein the operations further comprise: steps for filtering the captured infrared images.

13. The system of any one of embodiments 1-6, wherein the trained computer vision model is configured to: compute the first score based on an aggregation of classification scores respectively corresponding to the captured infrared images; rank the captured infrared images based on the respective classification scores; and identify one or more infrared images from the captured infrared images having a largest classification score contributing to the computed first score, wherein the operations further comprise: obtaining, from the trained computer vision model, the one or more infrared images each including an indication of the respective classification score.

14. The system of embodiment 13, wherein the operations further comprise: extracting, for each of the one or more infrared images, values of gradients generated by a last layer of the trained computer vision model; encoding the values of the gradients for each respective infrared image to represent the values of the gradients as a heat map; and generating the heat map representing the respective infrared image based on the encoded values, wherein: regions representing subsets of the values of the gradients within a first gradient value range are depicted using a first color, regions representing subsets of the values of the gradients within a second gradient value range are depicted using a second color, and at least one value included in the first gradient value range is greater than values included in the second gradient value range.

15. The system of any one of embodiments 1-6, wherein the wearable fundus camera further comprises: a volume defined by a case of the wearable fundus camera when worn by the human; a head strap configured to bias the eye cuff against the face of the human; and a visible-light sensor configured to detect visible light leaking into the volume from an ambient environment of the human, wherein responsive to detecting more than a threshold amount of visible light, the visible light sensor outputs a signal to cause the computing system to differentiate a polarization of the visible light backscattered from the retina of the human and included within the captured infrared images.

16. The system of any one of embodiments 1-6, wherein the wearable fundus camera further comprises: a light emitting diode (LED) that outputs light of a visible wavelength to direct a focus of a pupil of an eye of the human towards a location of the LED such that the infrared light is directed toward a center of the pupil of the eye; and a beam splitter positioned to reflect the infrared light onto the retina and transmit light returning from the retina through the beam splitter to the image sensor.

17. A non-transitory computer-readable medium storing computer program instructions that, when executed by a computing system, effectuate operations comprising: obtaining, with a computing system, from a wearable device comprising an infrared light source configured to output infrared light directed at a retina of a human and an image sensor configured to capture, based on the infrared light, infrared images depicting the retina of the human, the captured infrared images depicting the retina of the human; obtaining, with the computing system, a trained computer vision model configured to detect ophthalmologic abnormalities in infrared images depicting retinas, wherein the trained computer vision model is: trained on a corpus of images comprising images depicting a plurality of objects, each of the plurality of objects being classified into one or more first categories of a first plurality of categories, wherein each image from the corpus of images includes one or more first labels, each of the one or more first labels indicating that a respective image has been classified into one of the one or more first categories, trained on a set of images comprising images depicting a plurality of retinas, each of the plurality of retinas being classified into one or more second categories of a second plurality of categories, wherein each image from the set of images includes one or more second labels, each of the one or more second labels indicating that a respective image has been classified into one of the one or more second categories, wherein each of the second plurality of categories include a subset of images from the set of images depicting a type of ophthalmologic abnormality or ophthalmologic normality, the type of ophthalmologic abnormality being one of a plurality of ophthalmologic abnormalities, and trained on a set of infrared images comprising infrared images depicting retinas, wherein each infrared image from the set of infrared images is classified into at least one of the second plurality of categories, wherein each infrared image from the set of infrared images includes at least one of the one or more second labels; providing, with the computing system, the captured infrared images, as input, to the trained computer vision model; obtaining, with the computing system, from the trained computer vision model, based on the captured infrared images, a first score indicating a likelihood that the retina depicted by the captured infrared images includes one of the plurality of ophthalmologic abnormalities; determining, with the computing system, whether the first score satisfies a threshold condition, wherein the threshold condition being satisfied comprises the first score being greater than or equal to a first threshold score; and storing, with the computing system, in memory, a result of the determination, wherein the result indicates whether the retina depicts one of the plurality of ophthalmologic abnormalities or the ophthalmologic normality.

18. A non-transitory computer-readable medium storing computer program instructions that, when executed by a computing system, effectuate operations comprising: obtaining, with the computing system, infrared images depicting a retina of a human; obtaining, with the computing system, a trained computer vision model configured to detect ophthalmologic abnormalities in infrared images depicting retinas, wherein the trained computer vision model is: trained on a corpus of images comprising images depicting a plurality of objects, each of the plurality of objects being classified into one or more first categories of a first plurality of categories, wherein each image from the corpus of images includes one or more first labels, each of the one or more first labels indicating that a respective image has been classified into one of the one or more first categories, trained on a set of images comprising images depicting a plurality of retinas, each of the plurality of retinas being classified into one or more second categories of a second plurality of categories, wherein each image from the set of images includes one or more second labels, each of the one or more second labels indicating that a respective image has been classified into one of the one or more second categories, wherein each of the second plurality of categories include a subset of images from the set of images depicting a type of ophthalmologic abnormality or ophthalmologic normality, the type of ophthalmologic abnormality being one of a plurality of ophthalmologic abnormalities, and trained on a set of infrared images comprising infrared images depicting retinas, wherein each infrared image from the set of infrared images is classified into at least one of the second plurality of categories, wherein each infrared image from the set of infrared images includes at least one of the one or more second labels; providing, with the computing system, the captured infrared images, as input, to the trained computer vision model; obtaining, with the computing system, from the trained computer vision model, based on the captured infrared images, a first score indicating a likelihood that the retina depicted by the captured infrared images includes one of the plurality of ophthalmologic abnormalities; determining, with the computing system, whether the first score satisfies a threshold condition, wherein the threshold condition being satisfied comprises the first score being greater than or equal to a first threshold score; and storing, with the computing system, in memory, a result of the determination, wherein the result indicates whether the retina depicts one of the plurality of ophthalmologic abnormalities or the ophthalmologic normality.

19. A method, comprising the operations of any one of embodiments 1-18.

What is claimed is:
1. An system, comprising:
a wearable fundus camera configured to be worn as a headset by a human, the wearable fundus camera comprising:
an infrared light source configured to output infrared light to be directed at a retina of the human;
an image sensor configured to capture infrared images depicting a retina of an eye of the human under illumination from the infrared light source without a pupil of the eye being dilated with mydriatics; and
an eye cuff configured to be biased against a face of the human and occlude at least some ambient light from reaching the image sensor;
a computing system storing computer program instructions that, when executed by the computing system, effectuate operations comprising:
obtaining at least some of the captured infrared images depicting the retina of the human;
obtaining access to a trained computer vision model configured to detect ophthalmologic abnormalities in retinal images;
providing the at least some of the captured infrared images, as input, to the trained computer vision model;
obtaining, from the trained computer vision model, based on the at least some of the captured infrared images, a first score indicating whether the at least some of the captured infrared images depict an ophthalmologic abnormality and storing, in memory, a result of the based on the score.

2. The system of claim 1, wherein the operations comprise:
pretraining the computer vision model with a first training set of images to form a pre-trained computer vision model, at least 50% of the images in the first training set not being retinal images;
training the pre-trained computer vision model with a second training set of labeled images, at least half of the labeled images in the second training set not being retinal images labeled according to whether the respective labeled images depict retinopathy; and
determining the first score.

3. The system of claim 1, wherein:
the trained computer vision model is trained on a corpus of images comprising images depicting a plurality of objects, each of the plurality of objects being classified into one or more first categories of a first plurality of categories, wherein each image from the corpus of images includes one or more first labels, each of the one or more first labels indicating that a respective image has been classified into one of the one or more first categories,
the trained computer vision model is trained on a set of images comprising images depicting a plurality of retinas, each of the plurality of retinas being classified into one or more second categories of a second plurality of categories, wherein each image from the set of images includes one or more second labels, each of the one or more second labels indicating that a respective image has been classified into one of the one or more second categories, wherein each of the second plurality of categories include a subset of images from the set of images depicting a type of ophthalmologic abnormality or ophthalmologic normality, the type of ophthalmologic abnormality being one of a plurality of ophthalmologic abnormalities, and
the trained computer vision model is trained on a set of infrared images comprising infrared images depicting retinas, wherein each infrared image from the set of infrared images is classified into at least one of the second plurality of categories, wherein each infrared image from the set of infrared images includes at least one of the one or more second labels.

4. The system of claim 1, wherein the wearable fundus camera weighs less than 2 kilograms and has a center of mass less than 10 centimeters from a portion of the eye cuff configured to be positioned adjacent a bridge of the human's nose when worn by the human.

5. The system of claim 1, wherein the wearable fundus camera further comprises:
one or more actuators configured to orient the infrared light source, wherein the infrared light source is oriented in response to determining that the infrared light is directed to a pupil of an eye of the human when the wearable fundus camera is worn by the human, wherein the operations further comprise:
identifying, based on at least one captured infrared image from the captured infrared images, using a first classifier configured detect an eye within an infrared image, a set of pixels representing a first portion of the at least one captured infrared image depicting the eye of the human;
identifying, using a second classifier configured to detect the pupil within the at least one captured infrared image, a subset of pixels from the set of pixels representing a second portion of the at least one captured infrared image depicting the pupil of the eye of the human, wherein the first portion of the at least one captured infrared image comprises the second portion of the at least one captured infrared image; and
determining, based on the subset of pixels, a location of the center of the pupil; and
causing the one or more actuators to adjust a position of the infrared light source such that the infrared light output by the infrared light source is directed at the location of the center of the pupil.

6. The system of claim 1, wherein the operations further comprise:
providing one or more additional captured infrared images to one or more binary classifiers, wherein the one or more additional captured infrared images are captured prior to the image sensor capturing the infrared images, wherein each of the one or more binary classifiers is configured to detect whether the retina depicted by the captured infrared images represents a respective contraindicator from a set of contraindicators;
preventing the one or more additional captured infrared images from being analyzed by the trained computer vision model in response to detecting a given contraindicator; and
causing the image sensor to capture the infrared images.

7. The system of claim 1, wherein the wearable fundus camera comprises at least part of the computer system.

8. The system of claim 1, wherein the infrared light includes incoherent light of multiple infrared wavelengths, the operations further comprise:
selecting, for each of the multiple infrared wavelengths, a subset of the captured infrared images, wherein each subset of the captured infrared images includes infrared images of a respective infrared wavelength, wherein providing the captured infrared images to the trained computer vision model comprises:
providing each subset of the captured infrared images to the trained computer vision model, wherein the first score is computed based on a weighted combination of a score output by the trained computer vision model for each subset of the captured infrared images.

9. The system of claim 1, wherein the image sensor captures a plurality of infrared images, the captured infrared images being some of the plurality of infrared images, wherein the wearable fundus camera further comprises:
memory storing additional computer program instructions; and
one or more processors that, in response to executing the additional computer program instructions, effectuate additional operations comprising:
providing the plurality of infrared images to a classifier trained to detect whether a given image depicts a retina of a human; and
filtering the plurality of infrared images based on results of the classifier to obtain the infrared images.

10. The system of claim 1, wherein the wearable fundus camera further comprises:
one or more computer processors configured to:
compute a blur score for each infrared image of the captured infrared images, wherein the blur score indicates how blurry a respective infrared image is, the blur score being computed by:

transforming a given infrared image into a grayscale infrared image, applying a Laplacian kernel to an array of pixel values representing the grayscale infrared image, and computing a variance of each pixel value from the array of pixel values, and generating, for the given infrared image, the blur score based the variance of each pixel value from the array of pixel values;

determine whether a respective blur score is satisfies a threshold;

removing one or more infrared images from the captured infrared images in response to determining that the respective blur score of the one or more infrared images satisfies the threshold.

11. The system of claim 1, wherein the wearable fundus camera further comprises:

means for outputting visible light directed at the retina of the human; and means for capturing a set of visible-light images depicting the retina of the human, wherein the score is further determined based on the set of visible-light images.

12. The system of claim 1, wherein the operations further comprise:

steps for filtering the captured infrared images.

13. The system of claim 1, wherein the trained computer vision model is configured to:

compute the first score based on an aggregation of classification scores respectively corresponding to the captured infrared images;

rank the captured infrared images based on the respective classification scores; and identify one or more infrared images from the captured infrared images having a largest classification score contributing to the computed first score, wherein the operations further comprise:

obtaining, from the trained computer vision model, the one or more infrared images each including an indication of the respective classification score.

14. The system of claim 13, wherein the operations further comprise:

extracting, for each of the one or more infrared images, values of gradients generated by a last layer of the trained computer vision model;

encoding the values of the gradients for each respective infrared image to represent the values of the gradients as a heat map; and generating the heat map representing the respective infrared image based on the encoded values, wherein:

regions representing subsets of the values of the gradients within a first gradient value range are depicted using a first color, regions representing subsets of the values of the gradients within a second gradient value range are depicted using a second color, and at least one value included in the first gradient value range is greater than values included in the second gradient value range.

15. The system of claim 1, wherein the wearable fundus camera further comprises:

a volume defined by a case of the wearable fundus camera when worn by the human;

a head strap configured to bias the eye cuff against the face of the human; and a visible-light sensor configured to detect visible light leaking into the volume from an ambient environment of the human, wherein responsive to detecting more than a threshold amount of visible light, the visible light sensor outputs a signal to cause the computing system to differentiate a polarization of the visible light backscattered from the retina of the human and included within the captured infrared images.

16. The system of claim 1, wherein the computing system comprises:

means for executing the trained computer vision model on a mobile computing device.

17. The system of claim 1, wherein the operations further comprise:

steps for performing data normalization for the captured infrared images.

18. The system of claim 1, wherein the operations further comprise:

steps for training the computer vision model.

19. The system of claim 1, wherein the operations further comprise:

steps for determining whether the at least some infrared images depict retinopathy.

20. The system of claim 1, wherein the wearable fundus camera further comprises:

a light emitting diode (LED) that outputs light of a visible wavelength to direct a focus of a pupil of an eye of the human towards a location of the LED such that the infrared light is directed toward a center of the pupil of the eye; and a beam splitter positioned to reflect the infrared light onto the retina and transmit light returning from the retina through the beam splitter to the image sensor.

21. A non-transitory computer-readable medium storing computer program instructions that, when executed by a computing system, effectuate operations comprising:

obtaining, with a computing system, from a wearable device comprising an infrared light source configured to output infrared light directed at a retina of a human and an image sensor configured to capture, based on the infrared light, infrared images depicting the retina of the human, the captured infrared images depicting the retina of the human;

obtaining, with the computing system, a trained computer vision model configured to detect ophthalmologic abnormalities in infrared images depicting retinas, wherein the trained computer vision model is:

trained on a corpus of images comprising images depicting a plurality of objects, each of the plurality of objects being classified into one or more first categories of a first plurality of categories, wherein each image from the corpus of images includes one or more first labels, each of the one or more first labels indicating that a respective image has been classified into one of the one or more first categories, trained on a set of images comprising images depicting a plurality of retinas, each of the plurality of retinas being classified into one or more second categories of a second plurality of categories, wherein each image from the set of images includes one or more second labels, each of the one or more second labels indicating that a respective image has been classified into one of the one or more second categories, wherein each of the second plurality of categories include a subset of images from the set of images depicting a type of ophthalmologic abnormality or ophthalmologic normality, the type of ophthalmologic abnormality being one of a plurality of ophthalmologic abnormalities, and trained on a set of infrared images comprising infrared images depicting retinas, wherein each infrared image from the set of infrared images is classified into at least one of the second plurality of categories, wherein each infrared image from the set of infrared images includes at least one of the one or more second labels;

providing, with the computing system, the captured infrared images, as input, to the trained computer vision model;

obtaining, with the computing system, from the trained computer vision model, based on the captured infrared images, a first score indicating a likelihood that the retina depicted by the captured infrared images includes one of the plurality of ophthalmologic abnormalities;

determining, with the computing system, whether the first score satisfies a threshold condition, wherein the threshold condition being satisfied comprises the first score being greater than or equal to a first threshold score; and storing, with the computing system, in memory, a result of the determination, wherein the result indicates whether the retina depicts one of the plurality of ophthalmologic abnormalities or the ophthalmologic normality.

22. A non-transitory computer-readable medium storing computer program instructions that, when executed by a computing system, effectuate operations comprising:

obtaining, with the computing system, infrared images depicting a retina of a human;

obtaining, with the computing system, a trained computer vision model configured to detect ophthalmologic abnormalities in infrared images depicting retinas, wherein the trained computer vision model is:

trained on a corpus of images comprising images depicting a plurality of objects, each of the plurality of objects being classified into one or more first categories of a first plurality of categories, wherein each image from the corpus of images includes one or more first labels, each of the one or more first labels indicating that a respective image has been classified into one of the one or more first categories, trained on a set of images comprising images depicting a plurality of retinas, each of the plurality of retinas being classified into one or more second categories of a second plurality of categories, wherein each image from the set of images includes one or more second labels, each of the one or more second labels indicating that a respective image has been classified into one of the one or more second categories, wherein each of the second plurality of categories include a subset of images from the set of images depicting a type of ophthalmologic abnormality or ophthalmologic normality, the type of ophthalmologic abnormality being one of a plurality of ophthalmologic abnormalities, and trained on a set of infrared images comprising infrared images depicting retinas, wherein each infrared image from the set of infrared images is classified into at least one of the second plurality of categories, wherein each infrared image from the set of infrared images includes at least one of the one or more second labels;

providing, with the computing system, the captured infrared images, as input, to the trained computer vision model;

obtaining, with the computing system, from the trained computer vision model, based on the captured infrared images, a first score indicating a likelihood that the retina depicted by the captured infrared images includes one of the plurality of ophthalmologic abnormalities;

determining, with the computing system, whether the first score satisfies a threshold condition, wherein the threshold condition being satisfied comprises the first score being greater than or equal to a first threshold score; and storing, with the computing system, in memory, a result of the determination, wherein the result indicates whether the retina depicts one of the plurality of ophthalmologic abnormalities or the ophthalmologic normality.

* * * * *